US010098987B2

(12) United States Patent
Ahlering et al.

(10) Patent No.: US 10,098,987 B2
(45) Date of Patent: *Oct. 16, 2018

(54) COATING FOR INTRALUMINAL EXPANDABLE CATHETER PROVIDING CONTACT TRANSFER OF DRUG MICRO-RESERVOIRS

(71) Applicant: M.A. Med Alliance SA, Mont-sur-Rolle (CH)

(72) Inventors: Michael Thomas Ahlering, Orange, CA (US); Ronald Kenichi Yamamoto, San Francisco, CA (US); Robert John Elicker, Rancho Santa Margarita, CA (US); Tien Thuy Nguyen, Daly City, CA (US); John Edwin Shulze, Singapore (SG); Jelle Jurjen Zoethout, La Sarraz (CH)

(73) Assignee: M.A. Med Alliance SA, Mont-sur-Rolle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/290,931

(22) Filed: Oct. 11, 2016

(65) Prior Publication Data
US 2017/0028105 A1 Feb. 2, 2017

Related U.S. Application Data

(63) Continuation of application No. 14/335,823, filed on Jul. 18, 2014, now Pat. No. 9,492,594.

(51) Int. Cl.
| | |
|---|---|
| *A61L 29/08* | (2006.01) |
| *A61M 25/10* | (2013.01) |
| *A61L 29/14* | (2006.01) |
| *A61L 29/12* | (2006.01) |
| *A61L 29/06* | (2006.01) |
| *A61K 31/43* | (2006.01) |
| *A61L 29/16* | (2006.01) |
| *A61K 31/436* | (2006.01) |

(52) U.S. Cl.
CPC ............ *A61L 29/08* (2013.01); *A61K 31/436* (2013.01); *A61L 29/06* (2013.01); *A61L 29/085* (2013.01); *A61L 29/12* (2013.01); *A61L 29/126* (2013.01); *A61L 29/14* (2013.01); *A61L 29/148* (2013.01); *A61L 29/16* (2013.01); *A61M 25/10* (2013.01); *A61M 25/1027* (2013.01); *A61L 2300/216* (2013.01); *A61L 2300/416* (2013.01); *A61L 2300/602* (2013.01); *A61L 2300/604* (2013.01); *A61L 2300/608* (2013.01); *A61L 2420/02* (2013.01); *A61L 2420/04* (2013.01); *A61L 2420/06* (2013.01); *A61M 2025/105* (2013.01); *A61M 2025/1031* (2013.01)

(58) Field of Classification Search
None
See application file for complete search history.

(56) References Cited

U.S. PATENT DOCUMENTS

| | | | |
|---|---|---|---|
| 4,546,097 A | * | 10/1985 | Pitha .................... C07J 71/0005 514/26 |
| 5,102,402 A | | 4/1992 | Dror et al. |
| 5,110,475 A | * | 5/1992 | Rossling .............. A61K 9/1277 210/321.78 |
| 5,879,713 A | | 3/1999 | Roth et al. |
| 5,893,840 A | | 4/1999 | Hull et al. |
| 5,954,706 A | | 9/1999 | Sahatjian |
| 6,129,705 A | | 10/2000 | Grantz et al. |
| 6,238,408 B1 | | 5/2001 | Kawabata et al. |
| 6,409,716 B1 | | 6/2002 | Sahatjian et al. |
| 6,419,692 B1 | | 7/2002 | Yang et al. |
| 6,461,644 B1 | | 10/2002 | Jackson et al. |
| 6,524,274 B1 | | 2/2003 | Rosenthal et al. |
| 6,560,897 B2 | | 5/2003 | Chickering, III et al. |
| 6,616,650 B1 | | 9/2003 | Rowe et al. |
| 6,656,156 B2 | | 12/2003 | Yang et al. |
| 6,706,034 B1 | | 3/2004 | Bhat |
| 6,776,796 B2 | | 8/2004 | Falotico et al. |
| 6,887,857 B2 | | 5/2005 | Naimark et al. |
| 6,923,996 B2 | | 8/2005 | Epstein et al. |
| 7,014,861 B2 | | 3/2006 | Roorda et al. |

(Continued)

FOREIGN PATENT DOCUMENTS

| | | |
|---|---|---|
| CN | 101019851 | 8/2007 |
| CN | 102485211 | 6/2012 |

(Continued)

OTHER PUBLICATIONS

Sato et al. Journal of Applied Polymer Science 2013 129:1607-1617; online Dec. 2012.*
Cayman Chemical Product information sheet 2012.*
An, et al.: "Laboratory methods for studies of bacterial adhesion," Journal of Microbiological Methods 30 (1997) 141-152.
Dos Santos, et al.: "Influence of poly(ethylene glycol) grafting density and polymer length on liposomes: Relating plasma circulation lifetimes to protein binding," Biochimica et Biophysica Acta, 2007 1768:1367-1377.

(Continued)

*Primary Examiner* — Robert A Wax
*Assistant Examiner* — Caralynne E Helm
(74) *Attorney, Agent, or Firm* — Knobbe Martens, Olson & Bear, LLP

(57) ABSTRACT

A coating for an expandable portion of a catheter comprising a hydrophobic matrix and a dispersed phase is disclosed. The dispersed phase comprises a plurality of micro-reservoirs dispersed in the hydrophobic matrix, wherein the plurality of micro-reservoirs comprises a first active agent and a first biodegradable or bioerodable polymer. A coating formulation and a method for forming the coating are also disclosed. A catheter comprising the coating on the expandable portion and a method for treating a condition are also provided.

44 Claims, 3 Drawing Sheets

(56) References Cited

U.S. PATENT DOCUMENTS

| | | | |
|---|---|---|---|
| 7,066,904 B2 | 6/2006 | Rosenthal et al. | |
| 7,169,404 B2 | 1/2007 | Hossainy et al. | |
| 7,402,172 B2 | 7/2008 | Chin et al. | |
| 7,514,099 B2 | 4/2009 | Chen et al. | |
| 7,572,245 B2 | 8/2009 | Herweck et al. | |
| 7,641,915 B2 | 1/2010 | Chen et al. | |
| 7,731,685 B2 | 6/2010 | Ragheb et al. | |
| 7,893,302 B2 | 2/2011 | Chen et al. | |
| 7,972,543 B2 | 7/2011 | Nakajima et al. | |
| 8,003,122 B2 | 8/2011 | Zhao | |
| 8,003,123 B2 | 8/2011 | Hossainy et al. | |
| 8,076,529 B2 | 12/2011 | Ehrenreich et al. | |
| 8,100,348 B2 | 1/2012 | Wissink et al. | |
| 8,158,106 B2 | 4/2012 | Guire et al. | |
| 8,162,880 B2 | 4/2012 | Jayaraman | |
| 8,241,921 B2 | 8/2012 | Slager et al. | |
| 8,246,576 B2 | 8/2012 | Slager et al. | |
| 8,277,868 B2 | 10/2012 | Kokish et al. | |
| 8,366,660 B2 | 2/2013 | Wang | |
| 8,403,910 B2 | 3/2013 | Wang | |
| 8,404,300 B2 | 3/2013 | Wang | |
| 8,414,909 B2 | 4/2013 | Wang | |
| 8,460,238 B2 | 6/2013 | Cheng et al. | |
| 8,696,644 B2 | 4/2014 | Baumbach et al. | |
| 8,715,230 B2 | 5/2014 | Baumbach et al. | |
| 2002/0032477 A1 | 3/2002 | Helmus et al. | |
| 2003/0064965 A1 | 4/2003 | Richter | |
| 2003/0129130 A1 | 7/2003 | Guire et al. | |
| 2004/0086542 A1 | 5/2004 | Hossainy et al. | |
| 2005/0008671 A1 | 1/2005 | Van Antwerp | |
| 2005/0060020 A1 | 3/2005 | Jenson | |
| 2005/0060028 A1 | 3/2005 | Horres et al. | |
| 2005/0192657 A1* | 9/2005 | Colen | A61F 2/82 623/1.11 |
| 2006/0025848 A1 | 2/2006 | Weber et al. | |
| 2006/0045901 A1 | 3/2006 | Weber | |
| 2007/0212386 A1 | 9/2007 | Patravale et al. | |
| 2007/0275027 A1 | 11/2007 | Wen et al. | |
| 2007/0299512 A1 | 12/2007 | Korzuschnik et al. | |
| 2008/0114096 A1 | 5/2008 | Qu et al. | |
| 2008/0181927 A1 | 7/2008 | Zhao et al. | |
| 2008/0206349 A1 | 8/2008 | Barnwell et al. | |
| 2008/0255509 A1 | 10/2008 | Wang et al. | |
| 2009/0112239 A1* | 4/2009 | To | A61M 25/1027 606/159 |
| 2009/0246252 A1 | 10/2009 | Arps et al. | |
| 2009/0263445 A1 | 10/2009 | Song | |
| 2010/0070013 A1 | 3/2010 | Park et al. | |
| 2010/0081992 A1 | 4/2010 | Ehrenreich et al. | |
| 2010/0076377 A1 | 5/2010 | Ehrenreich et al. | |
| 2010/0198150 A1 | 8/2010 | Michal et al. | |
| 2010/0203112 A1 | 8/2010 | Oh et al. | |
| 2010/0233236 A1 | 9/2010 | Zhao et al. | |
| 2010/0285085 A1* | 11/2010 | Stankus | A61L 29/085 424/423 |
| 2010/0324645 A1 | 12/2010 | Stankus et al. | |
| 2011/0143014 A1 | 6/2011 | Stankus et al. | |
| 2011/0144578 A1 | 6/2011 | Pacetti et al. | |
| 2011/0160659 A1 | 6/2011 | Clarke et al. | |
| 2011/0238011 A1 | 9/2011 | Scheller et al. | |
| 2012/0082706 A1 | 4/2012 | Nakagawa et al. | |
| 2012/0083734 A1* | 4/2012 | Ayres | A61L 29/085 604/103.02 |
| 2012/0128760 A1 | 5/2012 | Manoharan et al. | |
| 2012/0165786 A1 | 6/2012 | Chappa et al. | |
| 2012/0177742 A1 | 7/2012 | McClain et al. | |
| 2012/0225100 A1 | 9/2012 | Darcy et al. | |
| 2012/0277726 A1 | 11/2012 | Doshi et al. | |
| 2012/0277727 A1 | 11/2012 | Doshi et al. | |
| 2012/0296274 A1 | 11/2012 | Slager et al. | |
| 2012/0310210 A1 | 12/2012 | Campbell et al. | |
| 2012/0315300 A1 | 12/2012 | Doshi et al. | |
| 2012/0316496 A1* | 12/2012 | Hoffmann | A61L 29/085 604/103.02 |
| 2013/0123695 A1* | 5/2013 | Hoffmann | A61L 29/085 604/103.02 |
| 2013/0130910 A1 | 5/2013 | Hori et al. | |
| 2013/0190689 A1 | 7/2013 | Slager et al. | |
| 2013/0195920 A1 | 8/2013 | Maier et al. | |
| 2013/0197434 A1 | 8/2013 | Wang | |
| 2013/0197435 A1 | 8/2013 | Wang | |
| 2013/0197436 A1 | 8/2013 | Wang | |
| 2013/0209662 A1 | 8/2013 | Wang et al. | |
| 2013/0243867 A1 | 9/2013 | Mohapatra et al. | |
| 2014/0004170 A1 | 1/2014 | Kröhen et al. | |
| 2016/0015862 A1 | 1/2016 | Ahlering et al. | |

FOREIGN PATENT DOCUMENTS

| | | | |
|---|---|---|---|
| CN | 102936338 | 2/2013 | |
| EP | 1 872 809 B1 | 10/2011 | |
| KR | 101085203 B1 | 11/2011 | |
| RU | 2097038 C1 | 11/1997 | |
| WO | WO 2009/113605 A1 | 9/2009 | |
| WO | WO-2011044889 A1 * | 4/2011 | A61L 29/085 |
| WO | WO-2011147407 A2 * | 12/2011 | A61L 29/085 |
| WO | WO 2012/162061 | 11/2012 | |
| WO | WO 2012/164251 | 12/2012 | |
| WO | WO 2013/007653 | 1/2013 | |
| WO | WO 2013/014677 | 1/2013 | |
| WO | WO 2016/011298 | 1/2016 | |

OTHER PUBLICATIONS

Hickey, et al.: "Dexamethasone/PLGA microspheres for continuous delivery of an anti-flammatory drug for implantable medical devices," Biomaterials 23 (2002) 1649-1656.

Jones, et al.: "Characterisation and evaluation of novel Surfactant bacterial anti-adherent coatings for endotracheal tubes designed for the prevention of ventilator-associated pneumonia," Journal of Pharmacy and Pharmacology, 2003 55:43-52.

Kaufmann, et al.: "Characterisation of the structure of PEG-supported lipid bilayers," European Cells and Materials 2007 14(suppl. 3):53.

Siepmann et al., "Modeling of Drug Release from Delivery Systems Based on Hydroxypropyl methylcellulose (HPMC)," Advanced Drug Delivery Reviews vol. 48, pp. 139-157, 2001.

International Search Report and Written Opinion re PCT Application No. PCT/US2015/040812, dated Sep. 23, 2015.

International Written Opinion re PCT Application No. PCT/US2015/040812, dated Jun. 13, 2016.

International Preliminary Report on Patentability re PCT Application No. PCT/US2015/040812, dated Oct. 17, 2016.

Office Action received in Japanese Patent Application No. 2017-503950 dated Apr. 3, 2018 in 10 pages.

* cited by examiner

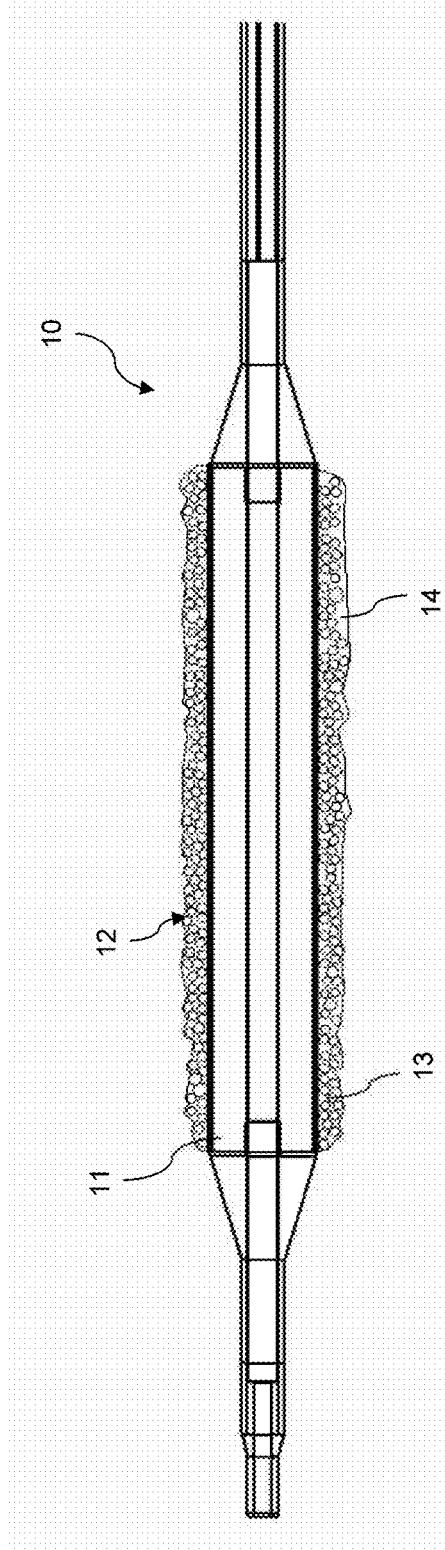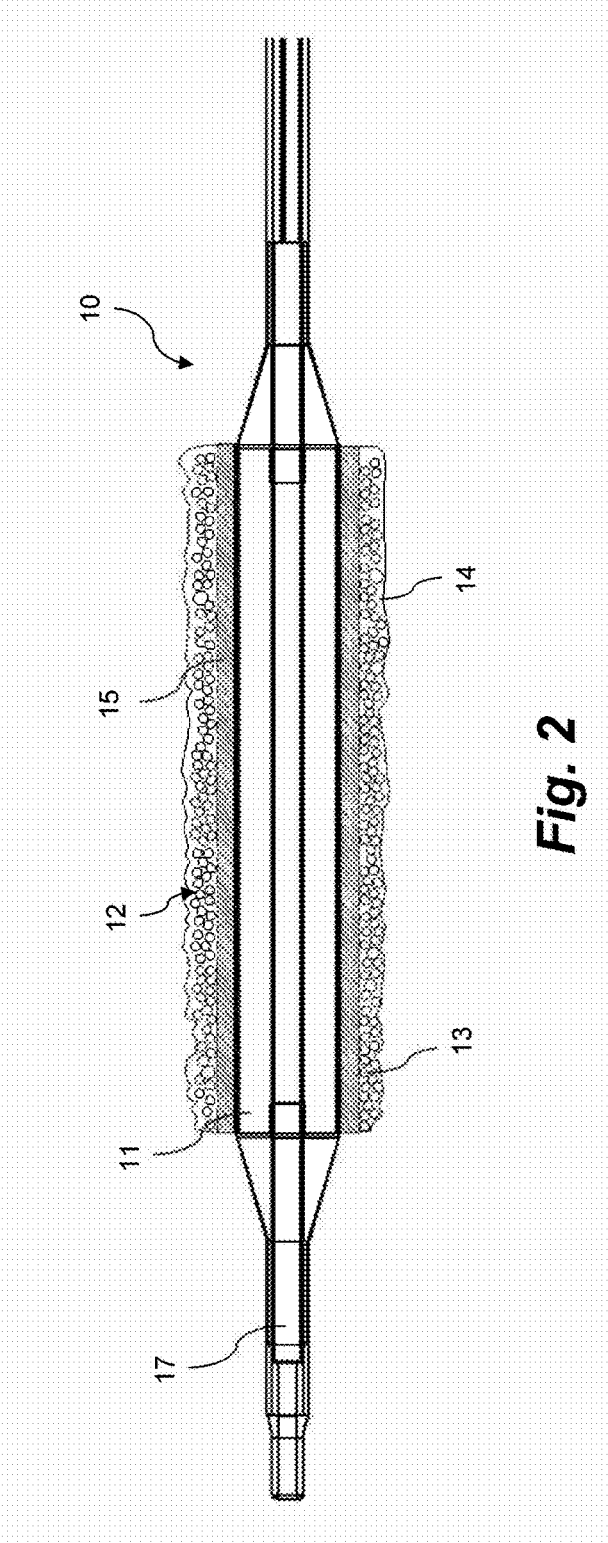
Fig. 1
Fig. 2

COATING FOR INTRALUMINAL EXPANDABLE CATHETER PROVIDING CONTACT TRANSFER OF DRUG MICRO-RESERVOIRS

CROSS-REFERENCES TO RELATED APPLICATIONS

This application is a continuation of U.S. patent application Ser. No. 14/335,823 filed Jul. 18, 2014, published as U.S. Patent Publication No. 2016/0015862. The entire disclosures of all the above mentioned applications, including all appendices and attachments, are hereby incorporated by reference for all purposes.

BACKGROUND OF THE INVENTION

Field of the Invention

This disclosure is related to the field of drug delivery via expandable catheters.

Description of the Related Art

Balloon angioplasty is an established method for the treatment of vascular disease by physically dilating an area of atherosclerosis, stenosis or reduction in luminal diameter in a diseased blood vessel. Angioplasty is typically performed with a catheter which may be advanced within the circulatory system to the diseased area. The catheter has a balloon at the distal end that is inflated to dilatate and expand the area of stenosis. In many cases, such as in the coronary arteries, a stent is also expanded on the exterior of the balloon. The stent is left in place after deflation and removal of the balloon to maintain the patency of the expanded lumen.

In order to achieve the physical enlargement of the vessel, large forces are exerted upon the tissues of the vessel during high pressure balloon inflation. The physical dilatation results in injury to the vessel, including endothelial disruption, fragmentation of the inner elastic lamina, and dissection of the vessel tunica media. Injury often extends into the outer adventitia as well. The biological response of the vessel progresses through a thrombotic phase during days 0 to 3, involving platelet activation and adhesion and thrombus formation. The thrombotic phase is followed by a cell recruitment phase during days 3 to 8 involving the infiltration of inflammatory cells, macrophages and lymphocytes, into the site of vessel damage. The release of growth factors and cytokines from the inflammatory cells lead to the proliferative phase during days 8 to day 14 in which the dormant smooth muscle cells in the tunica media of the vessel are stimulated to proliferate. Subsequently, the migration of the proliferating smooth muscle cells to the tunica intima and thrombus in the lumen results in neointimal hyperplasia, a primary component of restenosis. Although cell proliferation ceases after 14 days, continued production of extracellular matrix by the smooth muscle cells continues to increase the extent of neointimal hyperplasia and restenosis. The restenosis effectively reverses the dilatation treatment and potentially creates a critical threat to the patient. Human clinical studies have demonstrated that restenosis generally occurs 1 to 3 months after balloon angioplasty and the restenosis typically peaks at approximately 3 months.

Although balloon angioplasty provides a critical increase in blood flow in diseased vessels, restenosis is inherent due to the extent of associated mechanical injury. One strategy of reducing the restenosis response is to release drugs into the vessel in combination with the balloon dilatation treatment to counteract the inflammation and healing response. Approaches include the coating of the balloon with drugs, such as paclitaxel and sirolimus (rapamycin), which limit cellular proliferation. During contact of the balloon onto the luminal surface of the vessel it is believed that the coating facilitates transfer of the drug to the vessel injury site. These methods attempt to provide a drug concentration which is sufficient to reduce restenosis caused by cell proliferation and at the same time is low enough to minimize toxicity to the vessel that may result in damage or impairment of the vessel. It is believed that it is desirable to maintain an effective drug concentration for a sufficient time to minimize restenosis.

In practice, drug delivery to the tissues of the vessel wall by drug coated balloons as described in the art is limited by the short period of time during which the balloon may be placed in contact with the vessel. Typically the balloon inflation during angioplasty is performed for approximately 30 to approximately 120 seconds to limit cardiac ischemia and potential patient complications and discomfort. These short balloon inflation and drug delivery times may be sufficient for the antineoplastic drug paclitaxel which has demonstrated inhibition of neointimal formation in animals after a few minutes of exposure time. However, to provide maximum therapeutic effect and minimize potential high dose toxicity to the vessel, it would be desirable to provide delivery of drugs to the vessel over an extended period of time, ideally longer than the duration of balloon inflation. Additionally, drugs such as sirolimus and its analogues have both anti-proliferative and anti-inflammatory activity that may provide benefit beyond the acute period for restenosis if delivered over an extended time.

Many of the drug coated balloons described in the prior art use high initial levels of active agent and multiple treatments to create a high initial concentration, but then the concentration rapidly falls off. This is undesirable because most of the active agent on the device is lost as possible embolic particulate into the bloodstream, or by diffusion away from the treatment site.

Many of the drug coatings described in the prior art include hydrophilic polymers and excipients or excipients that are liquid at body temperature. Such hydrophilic coating formulations provide a hydrophilic matrix for the hydrophobic drug particles and may be effective at transferring the drug to the vessel wall. However, such coatings do not provide significant resistance to wash off from blood either during maneuvering of the balloon to the treatment site or after transfer of the drug coating to the vessel surface.

SUMMARY OF THE INVENTION

Some embodiments provide a coating for an expandable portion of a catheter comprising a hydrophobic matrix and a dispersed phase, wherein the dispersed phase comprises a plurality of micro-reservoirs dispersed in the hydrophobic matrix, wherein the plurality of micro-reservoirs comprises a first active agent intermixed with or dispersed in a first biodegradable or bioerodable polymer. Some embodiments provide a coating wherein the dispersed phase comprises a plurality of micro-reservoirs dispersed in the hydrophobic matrix wherein some of the plurality of micro-reservoirs comprises a first active agent and a first biodegradable or bioerodable polymer.

Some embodiments provide a catheter comprising an expandable portion on an elongated body and a coating as described herein over the expandable portion. In some embodiments, the catheter further comprises a release layer between the expandable portion and the coating, wherein the release layer is configured to release the coating from the expandable portion. In some embodiments, the catheter further comprises a protective coating over the coating.

Some embodiments provide a coating formulation for an expandable portion of a catheter comprising a solid portion and a fluid. The solid portion comprises a plurality of micro-reservoirs and at least one hydrophobic compound. The plurality of micro-reservoirs comprises a first active agent and a first biodegradable or bioerodable polymer.

Some embodiments provide a method for coating an expandable portion of a catheter comprising disposing a coating formulation described herein over the surface of an expanded expandable portion of a catheter, evaporating the fluid, and collapsing the expandable portion.

Some embodiments provide a method for treating or preventing a condition at a treatment site comprising advancing a catheter comprising an expandable portion to the treatment site, wherein the expandable portion is coated with a coating described herein, expanding the expandable portion to allow contact between the coating and a tissue at the treatment site, collapsing the expandable portion, and removing the catheter.

BRIEF DESCRIPTION OF THE DRAWINGS

Features and aspects, and advantages of the embodiments of the present disclosure are described in detail below with reference to the drawings of various embodiments, which are intended to illustrate and not to limit the invention. These drawings depict only several embodiments in accordance with the disclosure and are not to be considered limiting of its scope.

FIG. 1 depicts one embodiment of a balloon catheter with a coating on the expandable portion of the catheter.

FIG. 2 depicts one embodiment of a balloon catheter with a release layer between the coating and the expandable portion of the catheter.

DETAILED DESCRIPTION OF THE PREFERRED EMBODIMENT

Figure 3:
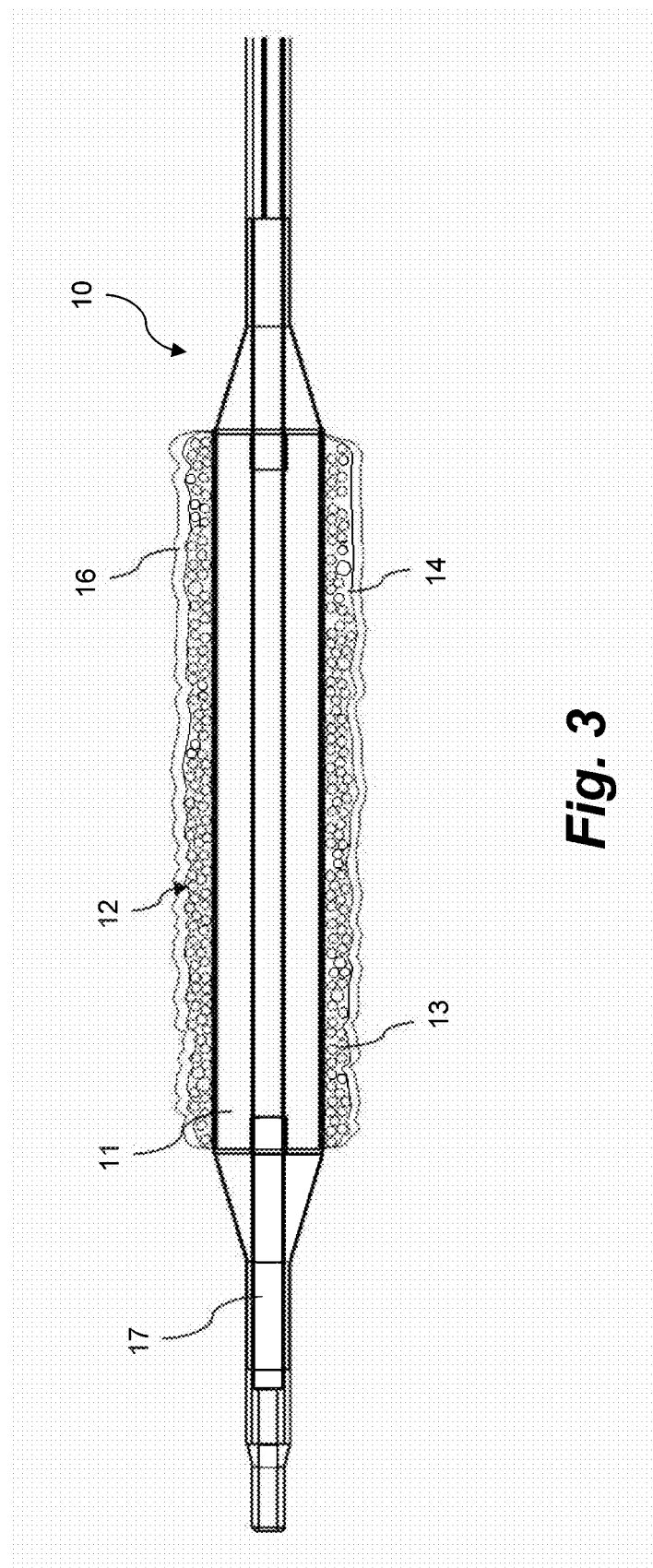
FIG. 3 depicts one embodiment of a balloon catheter with a protective layer over the coating.

To overcome the limitations of the prior art, the embodiments disclosed herein provide coatings for an expandable portion of a catheter that have time-release micro-reservoirs of drug intermixed with or dispersed within a coating on a balloon that can be transferred to the luminal surface of the vessel during the 30 to about 120 seconds balloon inflation time. This approach enables an extended and controlled release of drug over a longer period of time that may be tailored by the design of the micro-reservoirs for the characteristics of a particular drug or the pathology of the diseased vessel. In addition to providing sustained release, the coating disclosed herein also can resist blood wash off, which both increases drug transfer efficiency and patient safety from excessive particulate.

Coating

Disclosed herein is a coating for an expandable portion of a catheter or a catheter system. The catheter is designed for insertion into a living body for delivering at least one active agent locally. The coating is formulated and constructed for minimal solubilization and dispersion into the blood stream while the catheter is being positioned into the target vessel for treatment, or after transfer of the coating to the tissues of the vessel wall. In some embodiments, the active agent or drug is delivered to the vessel for preventing or minimizing restenosis after balloon angioplasty. In some embodiments, the expandable portion may be a balloon of a balloon catheter.

With reference to FIG. 1, in some embodiments, the coating 12 for an expandable portion 11 of a catheter 10 includes two phases, a hydrophobic matrix 14 and a dispersed phase 13. The dispersed phase 13 is dispersed in the hydrophobic matrix 14. The dispersed phase 13 includes a plurality of micro-reservoirs, and the plurality of micro-reservoirs include a first active agent and a first biodegradable or bioerodable polymer. In some embodiments, the first active agent is intermixed with or dispersed in the first biodegradable or bioerodable polymer. In some embodiments, some micro-reservoirs may comprise a first active agent and a biodegradable or bioerodable polymer. In some embodiments, the plurality of micro-reservoirs also include a second active agent. In some embodiments, the plurality of micro-reservoirs may further include a second biodegradable or bioerodable polymer. In some embodiments, the first and the second biodegradable or bioerodable polymer may be the same or different. In some embodiments, the plurality of micro-reservoirs may contain only one type of micro-reservoirs. In some embodiments, the coating 12 includes about 10% to about 75%, about 20% to about 65%, or about 30% to about 55% by weight of the plurality of micro-reservoirs. In some embodiments, the coating 12 has a surface concentration of about 1 $\mu g/mm^2$ to about 10 $\mu g/mm^2$, about 2 $\mu g/mm^2$ to about 9 $\mu g/mm^2$, or about 3 $\mu g/mm^2$ to about 8 $\mu g/mm^2$ on the expendable portion of the catheter 10.

The hydrophobic matrix 14 comprises a combination of materials selected for its desired adhesive properties to the luminal surface. Preferred hydrophobic matrix 14 includes a combination of hydrophobic compounds that are resistant to dissolution into blood but provides for uniform distribution of the formulation including the micro-reservoirs when applied to the surface of the balloon. In some embodiments, the hydrophobic matrix 14 includes at least one hydrophobic compound selected from the group consisting of sterols, lipids, phospholipids, fats, fatty acids, surfactants, and their derivatives. Particularly useful formulations are a combination of a sterol and a fatty acid or phospholipid. The sterol may be a sterol which utilizes the body's natural clearance mechanism such as by forming complexes with serum lipids or aggregates with serum apolipoproteins to provide transport to the liver for metabolic processing. In some embodiments, the sterol may be cholesterol. Due to the natural compatibility of cholesterol and fatty acids or phospholipids, such combinations may provide a homogenous mixture for coating 12 and a resulting homogenous coating on the balloon surface. The coating 12 formed by such combinations are homogenous without the formation of micelles or liposomes in the hydrophobic matrix 14.

In some embodiments, the hydrophobic matrix 14 includes a cholesterol and a fatty acid. In some embodiments, the weight ratio of cholesterol to fatty acid is in the range of about 1:2 to about 3:1, about 1:1.5 to about 2.5:1, or about 1:1 to about 2:1. The cholesterol component of the formulation may comprise cholesterol, chemically modified cholesterol or a cholesterol conjugate. In some embodiments, the cholesterol is dimethylaminoethane-carbamoyl cholesterol (DC-Cholesterol). For physiological compatibility, preferred fatty acids are fatty acids normally found in serum or cell membranes. In some embodiments, the fatty acid is selected from the group consisting of lauric acid, lauroleic acid, tetradeadienoic acid, octanoic acid, myristic acid, myristoleic acid, decenoic acid, decanoic acid, hexadecenoic acid, palmitoleic acid, palmitic acid, linolenic acid, linoleic acid, oleic acid, vaccenic acid, stearic acid, eicosapentaenoic acid, arachadonic acid, mead acid, arachidic acid, docosahexaenoic acid, docosapentaenoic acid, docosatetraenoic acid, docosenoic acid, tetracosanoic acid, hexacosenoic acid, pristanic acid, phytanic acid, and nervonic acid.

In some embodiments, the hydrophobic matrix 14 includes a cholesterol and a phospholipid. In some embodiments, the weight ratio of cholesterol to phospholipid is in the range of about 1:2 to about 3:1, about 1:1.5 to about 2.5:1, or about 1:1 to about 2:1. The cholesterol component of the formulation may comprise cholesterol, chemically modified cholesterol or a cholesterol conjugate. In some embodiments, the cholesterol is DC-Cholesterol. Preferred phospholipids are phospholipids normally found in serum or cell membranes. In some embodiments, the phospholipid is selected from the group consisting of phosphatidylcholine, phosphatidylethanolamine, phosphatidylserine, or phosphatidylinositol. In some embodiments, the phospholipid comprises an acyl chain length of about 20 to about 34 carbons. In some embodiments, the hydrophobic matrix 14 may further include a third active agent, which can be the same or different from the first active agent in the plurality of micro-reservoirs.

In some embodiments of the disclosure, the hydrophobic matrix 14 comprises only hydrophobic components such as lipids, sterols and fatty acids. In other words, in some embodiments, the hydrophobic matrix contains no hydrophilic polymers or hydrophilic excipients. In some embodiments of the disclosure, the hydrophobic matrix 14 comprises only hydrophobic components such as lipids, sterols and fatty acids, and no amphiphilic constituents are present. Preferably, the coating 12 and its components have a limited solubility in blood or analogues such as plasma or phosphate buffered saline. The use of cationic cholesterol or a cationic phospholipid in the formulation may provide additional chemical attraction of the hydrophobic matrix 14 to the vessel surface and potentially to the surface of the micro-reservoirs to increase the transfer of the coating 12 and resistance to dissolution into blood after transfer. Suitable cationic forms of cholesterol are modified at the 3 carbon position to attach a pendant tertiary or quaternary amine and include DC-Cholesterol. Suitable cationic forms of phospholipids include naturally occurring phospholipids and synthetic modifications of phospholipids such as phosphatidylethanolamine, dioleoylphosphatidylethanolamine (DOPE), and amine derivatives of phosphatidylcholine such as ethylphosphatidylcholine.

In some embodiments, the acyl chain length and degree of unsaturation of the phospholipid component of the hydrophobic matrix 14 can be used for tailoring the physical and chemical properties of the hydrophobic matrix 14. In some embodiments, long acyl chain lengths are selected to increase hydrophobicity of the phospholipid for adhesion to the vessel surface and to decrease solubility and wash-off due to blood flow exposure. The acyl chain length of fatty acids and fatty acid portion of phospholipids are described by shorthand notation with the number of carbons followed by a colon with the number of carbon-carbon double bonds. In the following description of phospholipids, both the generic or trivial name, the stereo specific numbering and shorthand notation is used for the first description of the compound. Acyl chain lengths of 20 to 34 carbons (C20 to C34) are suitable for use as a coating 12 component, with acyl chain lengths of 20 to 24 carbons (C20 to C24) particularly preferred. Although the present invention will also work with saturated acyl chains, one or more sites of unsaturation may provide an increased chain flexibility. Examples of preferred phospholipids include dieicosenoyl phosphatidylcholine (1,2-dieicosenoyl-sn-glycero-3-phosphocholine, C20:1 PC), diarachidonoyl phosphatidylcholine (1,2-diarachidoyl-sn-glycero-3-phosphocholine, C20:0 PC), dierucoyl phosphatidylcholine (1,2-dierucoyl-sn-glycero-3-phosphocholine, C22:1 PC), didocosahexaenoyl phosphatidylcholine (1,2-didocosahexaenoyl-sn-glycero-3-phosphocholine, C22:6 PC), heneicosenoyl phosphatidylcholine (1,2-heneicosenoyl-sn-glycero-3-phosphocholine, C21:1 PC) and dinervonyl phosphatidylcholine (1,2-dinervonoyl-sn-glycero-3-phosphocholine, C24:1 PC) In some embodiments, the phospholipids have a transition temperature at or above ambient temperature (20° C.) such that the hydrophobic matrix 14 constitutes a solid during storage.

The plurality of micro-reservoirs comprises an active agent and a polymer. The active agent may be referred to as a first active agent or a second active agent. The active agent is associated with the polymer in a way to provide slow or extended release of the active agent from the micro-reservoirs. In some embodiments, the active agent is intermixed with or dispersed in the biodegradable or bioerodable polymer. In some embodiments, the active agent may be encapsulated by the biodegradable or bioerodable polymer. In some embodiments, the plurality of micro-reservoirs may include a first active agent. In some embodiments, the plurality of micro-reservoirs may further include a second active agent. Suitable active agent may include antiproliferative or anti-inflammatory agents such as paclitaxel, sirolimus (rapamycin) and their chemical derivatives or analogues which are mTOR inhibitors, inhibitory RNA, inhibitory DNA, steroids and complement inhibitors. In some embodiments, the active agent is selected from the group consisting of paclitaxel, sirolimus, paclitaxel derivative, sirolimus derivative, paclitaxel analogues, sirolimus analogues, inhibitory RNA, inhibitory DNA, steroids, and complement inhibitors. In some embodiments, the active agent is about 10% to about 50%, about 15% to about 45%, about 20% to about 40%, or about 25% to about 35% by weight of the plurality of micro-reservoirs. The micro-reservoirs may include microparticles or microspheres. In some embodiments, polylactic-co-glycolic acid (PLGA) microspheres are well suited for incorporation of the active agent for sustained release up to approximately 50% by weight of the active agent in the microsphere.

In some embodiments, the plurality of micro-reservoirs has an average diameter of about 0.5 microns to about 8 microns, about 2 micron to about 6 microns, or about 3 microns to about 5 microns. In some embodiments, the micro-reservoirs are desired to have a size large enough to provide a sustained release of the active agent, approximately 1.5 micron or greater in diameter or average cross-sectional dimension for microparticles of non-uniform size. Smaller sizes of micro-reservoirs typically have an increased surface area to volume ratio and reduced diffusional pathway for the active agent that does not provide sufficient extended release. The maximum size of the micro-reservoirs is approximately the size of a red blood cell, about 6 microns to about 8 microns, to prevent embolization of capillaries due to any micro-reservoirs released into the blood stream during or subsequent to treatment. In some embodiments, the micro-reservoirs do not necessarily have affinity or adhesion to the vessel surface.

The biodegradable or bioerodable polymer can provide controlled and extended release of the active agent. The biodegradable or bioerodable polymer may be referred to as a first biodegradable or bioerodable polymer or a second biodegradable or bioerodable polymer. The polymer acts as a barrier to drug diffusion thereby providing a release profile tailored for the pharmacokinetics of the active agent acting on the treated vessel. For example, the active agent may be intermixed and distributed into a polymer in a solid solution. The polymer may provide controlled release by reducing active agent diffusion or by coupling drug release to biodegradation, dissolution or bioerosion of the polymer. In some embodiments, the biodegradable or bioerodable polymer is selected from the group consisting of polylactic acid, polyglycolic acid and their copolymers, polydioxanone, polycaprolactone, polyphosphazine, collagen, gelatin, chitosan, glycosoaminoglycans, and combination thereof. In some embodiments, the micro-reservoirs may also be microspheres or microparticles containing at least one active agent which treats the inflammation or healing response. In some embodiments, the plurality of micro-reservoirs may include a first biodegradable or bioerodable polymer. In some embodiments, the plurality of micro-reservoirs may include a second biodegradable or bioerodable polymer.

After contact of the coating 12 with the vessel wall, the kinetics of active agent release is controlled by the release of active agent from the micro-reservoirs into the surrounding medium, thereby making available a sustained elution of active agent to penetrate into the vessel wall. To provide significant active agent during the initial high risk period for restenosis following dilation, it is preferred that the active agent in the coating 12 be continuously released with a half-life release kinetics of about 2 weeks to about 6 weeks or greater. In some embodiments, the plurality of micro-reservoirs has active agent release kinetics with a half-life of at least 14 days.

The active agent release kinetics may be tailored by the characteristics of the micro-reservoirs. Two or more types of micro-reservoirs with different active agents or different release kinetics for the same active agent may be formulated into the coating 12 to tailor the treatment effect. In some embodiments, some active agent may be incorporated into the coating formulation outside of the micro-reservoirs to provide a rapid initial release of active agent to the vessel walls, allowing the micro-reservoirs to provide sufficient active agent to maintain effective tissue concentration of active agent for a prolonged period of time. Since the healing and resolution of inflammation in the region of dilation typically takes 4-12 weeks, it is desirable to have micro-reservoirs and coating 12 to elute active agent to provide therapeutic tissue levels for at least about 4 weeks to about 12 weeks following the treatment. In certain applications, such as very long, extensively diseased vessels, maintenance of active agent levels for longer than 4 to 12 weeks may be desirable to provide additional protection from the effects of less common late restenosis.

The release of active agent intermixed with or dispersed in a solid has been shown to follow Higuchi kinetics with decreasing active agent release over time. For spherical particles with active agent dispersed in a polymer, the active agent release kinetics also follows a power law of decreasing release rate, Korsmeyer-Peppas kinetic model, similar to the Higuchi equation. (J. Siepmanna J, Peppas NA, Modeling of active agent release from delivery systems based on hydroxypropyl methylcellulose (HPMC), Advanced Drug Delivery Reviews 48 (2001) 139-157). The release kinetics of active agent from such micro-reservoirs is well suited for treatment of the vessel wall post dilatation. The design and selection of micro-reservoirs with the appropriate release constant provides for rapid initial release of active agent with sustained active agent release and extended active agent residence in the vessel wall over longer time periods compared to devices of the prior art. The active agent release rate may be tailored by the solubility of the active agent in the micro-reservoir material and by adjusting microporosity of the micro-reservoir. The length of effective active agent delivery may be tailored by the selection of micro-reservoir size, active agent solubility in the micro-reservoir material, and amount of active agent loaded in the micro-reservoirs. The total amount of active agent to be delivered is determined by the amount of micro-reservoirs in the coating formulation and their level of active agent loading. As a result, the coating 12 is able to be formulated to have a concentration of active agent in the range of about 0.3 to about 3 µg per $mm^2$ of expandable portion 11 surface. The desired kinetics of active agent release from the coating 12 may be provided by a single type of micro-reservoir or alternatively by a mixture of micro-reservoirs with different size or release characteristics to provide the desired release profile to the vessel wall.

In some embodiments, the coating 12 further includes a PEG-lipid for increased hemocompatiblity. Since the coating 12 disclosed herein is designed to be transferred to the surface of a blood vessel and to remain there to release drug during the vessel healing period, hemocompatiblity of the coating 12 is desired. In addition to preventing dissolution of the coating 12 into the blood stream prior to healing of the vessel, it is desired to prevent initiation of significant clotting and the attachment of fibrin and platelets to the coating surface exposed to blood after transfer. The addition of a PEG-lipid to the composition of cholesterol and a phospholipid or fatty acid may be used to provide increased hemocompatiblity of the formulation. PEG grafted polymer surfaces have shown improved blood contact characteristics primarily by lowering the interfacial free energy and by the steric hindrance of the hydrated PEG chains on the surface. While not wishing to be bound to a particular theory of operation, it is believed that a small amount of PEG-lipid conjugate added to the composition may migrate to the blood interface surface after transfer, especially for PEG-lipids of relatively low molecular weight. The PEG chains are thereby able to lower the interfacial free energy at the blood interfacing surface. Since the coating material at the blood interface is a small portion of the total coating, a relatively small amount of PEG-lipid is required.

In some embodiments, the PEG-lipid is selected from the group consisting of 1,2-di stearoyl-sn-glycero-3-phosphoethanolamine-N-methoxy(polyethylene glycol)-350 (DSPE-mPEG350), 1,2-dipalmitoyl-sn-glycero-3-phosphoethanolamine-methoxy(polyethylene glycol)-350 (DPPE-mPEG350), 1,2-dioleoyl-sn-glycero-3-phosphoethanolamine-N-methoxy(polyethylene glycol)-350 (DOPE-mPEG350), 1,2-di stearoyl-sn-glycero-3-phosphoethanolamine-N-methoxy(polyethylene glycol)-550 (DSPE-mPEG550), 1,2-dipalmitoyl-sn-glycero-3-phosphoethanolamine-N-methoxy(polyethylene glycol)-550 (DPPE-mPEG550), and 1,2-dioleoyl-sn-glycero-3-phosphoethanolamine-N-methoxy(polyethylene glycol)-500 (DOPE-mPEG550). In some embodiments, the PEG-lipid is about 1% to about 30% by weight of the hydrophobic matrix 14 consisting of the combination of the cholesterol, the fatty acid or phospholipid and the PEG-lipid. In other embodiments, the PEG-lipid is about 2% to about 25%, about 3% to about 20%, or about 5% to about 10% by weight of the hydrophobic matrix 14. In some embodiments, the amount of PEG-lipid is about 12% or less.

In some embodiments, the coating 12 further includes one or more additives. In some embodiments, the one or more additives are independently selected from penetration enhancers and stabilizers. For example, the coating 12 may further include additives to enhance performance, such as penetration enhancers. The penetration enhancer can aid diffusion of the active agent into the vessel wall and maximize tissue delivery of the active agent. Suitable penetration enhancers may include surfactants, cationic excipients and cationic lipids. In some embodiments, the additive may be added to the hydrophobic matrix, the micro-reservoirs, or both. In some embodiments, stabilizers may be added to protect the drug during sterilization of the balloon catheter system and its subsequent storage before use. Stabilizers may include antioxidants and free radical scavengers. Examples of stabilizers include gallic acid, propylgallate, tocopherols and tocotrienols (Vitamin E), butylatedhydroxytoluene, butylatedhydroxyanisole, ascorbic acid, thioglycolic acid, ascorbyl palmitate, and EDTA.

In some embodiments, the coating 12 further comprises a third active agent, wherein the third active agent is outside of the micro-reservoirs or in the hydrophobic matrix 14. The third active agent may be the same or different from the first or the second active agent in the plurality of micro-reservoirs. However, since the active agent(s) are primarily contained in the micro-reservoirs and not in direct contact with the hydrophobic matrix 14, the need to solubilize or emulsify the active agent in the hydrophobic matrix 14 itself is obviated. Since the active agent(s) are primarily contained in the micro-reservoirs and not in contact with the hydrophobic matrix 14, the need to include an amphiphilic constituent or constituent with active agent affinity in the hydrophobic matrix 14 itself is obviated. The hydrophobic matrix 14 can therefore be optimized toward suitable properties for resistance to blood wash-off and adhesion to the vessel surface for coating 12 transfer.

Catheter

With reference to FIG. 2, disclosed herein is also a catheter 10 that includes an expandable portion 11 on an elongated body 17, a coating 12 as described above over the expandable portion 11, and a release layer 15 between the expandable portion 11 and the coating 12. In some embodiments, the release layer 15 is configured to release the coating 12 from the expandable portion 11. A release layer 15 which is immiscible with the coating 12 is preferred to maintain distinct layers. In some embodiments, PEG conjugated lipids are used as a release layer 15 as the degree of hydrophilicity and miscibility with the active agent coating 12 may be tailored by the selection of the lipid and the PEG chain length. In some embodiments, the release layer 15 is 1,2-distearoyl-sn-glycero-3-phosphoethanolamine-N-(methoxy(polyethylene glycol)-350) (DSPE-mPEG350) or 1,2-distearoyl-sn-glycero-3-phosphoethanolamine-N-(methoxy(polyethylene glycol)-550) (DSPE-mPEG550). In some embodiments, the release layer 15 has a surface concentration of about 0.1 µg/mm$^2$ to about 5 µg/mm$^2$, 0.25 µg/mm$^2$ to about 3 µg/mm$^2$, or 0.5 µg/mm$^2$ to about 2 µg/mm$^2$.

With reference to FIG. 3, in some embodiments, the catheter 10 further includes a protective layer 16 over the coating 12 as a top coat. In some embodiments, the protective layer 16 includes a hydrophilic polymer, a carbohydrate, or an amphiphilic polymer. In some embodiments, the protective layer 16 is a glycosaminoglycan or a crystalized sugar. Examples of glycosaminoglycans include dextran sulfate, chondroitin sulfate, heparan sulfate, and hyaluronic acid. Examples of crystalized sugars include mannitol, sorbitol, erythritol, and xylitol. The crystalline nature of these sugars provides a hard surface that protects the underlying micro-reservoirs. The thickness of the protective layer 16 can be adjusted such that the protective layer 16 washes away during the transit time required to advance the catheter 10 to the target site. In some embodiments, the protective layer 16 has a surface concentration of about 0.1 µg/mm$^2$ to about 5 µg/mm$^2$, about 0.2 µg/mm$^2$ to about 4 µg/mm$^2$, or about 0.3 µg/mm$^2$ to about 3 µg/mm$^2$.

The expandable portion 11 of the catheter 10 may be a balloon, which acts as a substrate for the coating 12. In some embodiments, the balloon may be of a low pressure design using an elastomeric material such as polyisoprene, polystyrene copolymers, polysiloxane, or polyurethane. In some embodiments, the balloon may also be of a high pressure design using high tensile strength polymers such as polyvinylchloride, polyethylene, polyethylene terephthalate, or nylon. In some embodiments, the expandable portion 11 may be made of Nylon 12. The coating 12 may be sufficiently adhered to the expandable portion 11, but is readily transferred to the tissues of the vessel lumen upon contact. In such cases, a release layer may be omitted. In addition, Nylon 12 has sufficient strength such that the balloon may further act as a post-dilatation balloon (if needed) in a subsequent procedure after transfer of the coating 12.

In some embodiments, the expandable portion 11 underneath the coating 12 may be used to dilate the target vessel. In some embodiments, the vessel may be pre-dilated with another balloon catheter 10 prior to treatment with the coated balloon of the present embodiments.

Coating Formulation

Disclosed herein is also a coating formulation for an expandable portion 11 of a catheter 10. The formulation includes a solid portion and a fluid. The solid portion includes a plurality of micro-reservoirs and at least one hydrophobic compound. The fluid acts to disperse or solubilize the at least one hydrophobic compound. In some embodiments, the fluid may disperse some hydrophobic compounds and solubilize other hydrophobic compounds. The micro-reservoirs are dispersed and suspended in the resultant fluid mixture to form the coating formulation. The fluid mixture is formulated to form a homogenous mixture of the hydrophobic compounds that does not separate during drying to result in a uniform, conformal coating of the hydrophobic matrix 14. The coating formulation is characterized by weight of the solid portion, which refers to all the non-volatile components of the coating formulation, but excludes the fluid that is subsequently evaporated during drying of the coating.

The micro-reservoirs include an active agent and a polymer. The active agent may be referred to as a first active agent or a second active agent as described herein. The polymer may be a first biodegradable or bioerodable polymer or a second biodegradable or bioerodable polymer described herein. In some embodiments, the active agent is intermixed with or dispersed in the biodegradable or bioerodable polymer described herein. In some embodiments, the formulation may include more than one type of micro-reservoirs. For example, the plurality of micro-reservoirs may include a first active agent and a first biodegradable or bioerodable polymer. In some embodiments, the plurality of micro-reservoirs may further include a second active agent.

In some embodiments, the plurality of micro-reservoirs may also include a second biodegradable or bioerodable polymer.

The micro-reservoirs may be fabricated by any of the known means for particle manufacture, including spray drying, coacervation, micromolding, and milling. All such processes begin by dissolving the active agent and the polymer together in a suitable solvent such as acetonitrile or dichloromethane, then removing the solvent in a controlled manner that creates uniform particles. The particles may be further shaped by mechanical means. Processes that produce particles with size distributions with coefficients of variation of 10% or less are particularly useful for providing more consistent active agent release rates. Methods for producing microspheres of uniform size are described by forming an emulsion of the microsphere material and extruding the emulsion through a substrate with through-holes of controlled size as described in U.S. Pat. No. 7,972,543 and U.S. Pat. No. 8,100,348. Alternatively, microspheres may be produced by spray-drying solutions of polymers as described in U.S. Pat. No. 6,560,897 and US 20080206349.

The fluid of the coating formulation may comprise water, organic solvent, perfluorocarbon fluids, or a mixture of such fluids. In some embodiments, the fluid is selected from the group consisting of pentane, hexane, heptane, heptane and fluorocarbon mixture, alcohol and fluorocarbon mixture, and alcohol and water mixture. Fluids which readily solubilize the active agent or the polymer of the micro-reservoirs are not preferred since they may extract the active agent from the micro-reservoirs. Such non-preferred fluids include acetic acid, acetonitrile, acetone, dichloromethane, ethyl formate, cyclohexanone, DMSO, and chloroform. Optionally, the fluid/fluid blend may be selected to saturate at the desired level of extracted active agent. Additional active agent that is the same as the one in the micro-reservoirs may be added to the fluid in advance to presaturate the solution, thereby reducing extraction from the micro-reservoirs during processing of the coating.

In some embodiments, the at least one hydrophobic compound is selected from the group consisting of sterols, lipids, phospholipids, fats, fatty acids, and surfactants, and their derivatives. In some embodiments, the at least one hydrophobic compound comprises a cholesterol and a fatty acid as described herein. In other embodiments, the at least one hydrophobic compound comprises a cholesterol and a phospholipid as described herein. In some embodiments, the formulation can also include a PEG-lipid as described herein. In some embodiments, the formulation can further include additives like penetration enhancers and stabilizers.

In some embodiments, the solid portion further includes a third active agent outside of the plurality of micro-reservoirs. In other words, the coating formulation can lead to a hydrophobic matrix 14 that further comprises the third active agent. The active agent outside of the micro-reservoirs may be the same or different from the active agent(s) in the micro-reservoirs. In some embodiments, the solid portion may further comprise a PEG-lipid. In some embodiments, the solid portion may also further comprise an additive described herein.

In some embodiments, the concentration of the solid portion by percent weight in the coating formulation is approximately 1% to approximately 90%. In some embodiments, the solids content of the coating formulation has a concentration of about 2% to about 80% by weight, about 3% to about 70% by weight, or about 4% to about 60% by weight. In some embodiments for spray coating, the solid portion of the coating formulation has a concentration of about 2% to about 7% by weight. The solid portion of the coating formulation comprises about 10% to about 75%, about 20% to about 65%, or about 30% to about 55% by weight of the plurality of micro-reservoirs.

Method for Coating

Disclosed herein is also a method for coating an expandable portion 11 of a catheter 10. The steps include, disposing a formulation described herein over the surface of an expanded expandable portion 11 of a catheter 10, evaporating the fluid constituents of the coating formulation, and collapsing the expandable portion 11. Disposing a formulation over the surface of an expanded expandable portion 11 includes disposing the formulation on the surface of an expanded expandable portion 11. In some embodiments, the formulation can be disposed on or over the expanded expandable portion 11 by spray coating, dip coating, roll coating, electrostatic deposition, printing, pipetting, or dispensing.

The coating formulation is prepared by mixing the coating components in a fluid as disclosed herein. In some embodiments, the micro-reservoirs are dispersed into the fluid formulation. Once fully mixed, the coating formulation may be applied to the surface of the expanded expandable portion 11 such as a balloon and let dry to form the coating 12. The application of the coating formulation may be repeated as necessary to deposit the desired amount of coating 12, usually in the range of about 5 mg to about 9 mg of coating 12 per $mm^2$ of the balloon surface. The coating 12 is allowed to dry and the balloon deflated and folded to allow introduction into the vascular system.

In some embodiments, the method may further comprise disposing a release layer on the surface of an expanded expandable portion 11. As such, the coating formulation would be disposed on the release layer, while the release layer is disposed onto the surface of the expanded expandable portion 11. The release layer is described above.

Method for Treating or Preventing a Condition

Disclosed herein is also a method for treating or preventing a condition at a treatment site. The method involves the steps of advancing a catheter 10 comprising an expandable portion 11 to the treatment site, expanding the expandable portion 11 to allow contact between the coating 12 and a tissue at the treatment site, collapsing the expandable portion 11, and removing the catheter 10. The expandable portion 11 is coated with a coating described herein. In some embodiments, the contact between the tissue and the coating 12 results in a transfer of at least a portion of a coating on the expandable portion 11 to the treatment site during contact for a period of from about 30 to about 120 seconds.

A catheter 10 with expandable portion 11 such as a coated balloon catheter is used here to demonstrate the concept of delivering an active agent or a combination of active agents to a vessel. The coated balloon catheter is introduced into a vessel with the expandable portion 11 folded to provide a small cross-sectional profile and to facilitate percutaneous insertion of the catheter 10, for example by the well-known Seldinger technique. After the expandable portion 11 of the catheter 10 is advanced to the diseased area of the vessel for treatment, the balloon is inflated, and the coating 12 makes firm contact with the vessel lumen. The coating is formulated to have affinity to the luminal tissue surface, resulting in adhesion of a layer of the coating on the vessel lumen. The expandable portion 11 may be inflated or expanded for a period of 30 seconds up to 2 minutes to promote adhesion and provide for initial active agent penetration into the vessel. The expandable portion 11 may be deflated and inflation repeated as desired for treatment to manage the time period and risks of vessel occlusion or tissue ischemia.

The coating is adhesively transferred to the lumen of the vessel upon balloon inflation and firm contact of the balloon surface to the vessel luminal surface. The adhesion of the coating to the vessel surface thereby carries the micro-reservoirs and transfers them to the vessel surface.

In some embodiments, the condition is selected from the group consisting of atherosclerosis, stenosis or reduction in luminal diameter in a diseased blood vessel, restenosis, and in-stent restenosis. In some embodiments, an additional release layer as described herein is disposed between the expandable portion 11 and the coating 12.

While the present disclosure is directed at the treatment of restenosis associated with balloon dilatation of blood vessels, the invention may be used to deliver drugs to various other lumens and hollow structures of the body such as the structures of the respiratory system, gastrointestinal system, urinary system, reproductive system, and lymphatic system. The coated device may be an inflatable balloon or other inflatable device. Alternatively the device delivering the coating of the present invention may be a non-inflatable device or any other type of expandable device that is used for treatment of a living body.

EXAMPLES

Example 1

Drug Containing Micro-Reservoirs (Microspheres) sphere s) fabricated by coacervation of polylactic-co-glycolic acid copolymer incorporating sirolimus (rapamycin) were obtained.

Microsphere sample 1: 50% DL-lactide/50% glycolide copolymer, average diameter 3.1 µm, SD 0.44 µm, 39% rapamycin by weight Microsphere sample 2: 75% DL-lactide/25% glycolide copolymer, average diameter 3.2 µm, SD 0.76 µm, 40% rapamycin by weight Microsphere sample 3: 50% DL-lactide/50% glycolide copolymer, average diameter 2.7 µm, SD 0.8 µm, 45% rapamycin by weight Microsphere sample 4: 75% DL-lactide/25% glycolide copolymer, average diameter 3.3 µm, SD 1.2 µm, 46% rapamycin by weight Microsphere sample 5: 75% DL-lactide/25% glycolide copolymer, average diameter 4.1 µm, SD 0.61 µm, 25% rapamycin by weight Microsphere sample 6: 75% DL-lactide/25% glycolide copolymer, average diameter 3.78 µm, SD 0.44 µm, 28.8% rapamycin by weight Microsphere sample 7: 75% DL-lactide/25% glycolide copolymer, average diameter 3.8 µm, SD 0.34 µm, 27.7% rapamycin by weight Microsphere sample 8: 75% DL-lactide/25% glycolide copolymer, average diameter 3.79 µm, SD 0.39 µm, 29.4% rapamycin by weight Drug content of these micro-reservoirs was verified by HPLC quantitation method. Typically, micro-reservoirs (1 to 5 mg) were weighed and dissolved in 1 ml acetonitrile, agitated gently at room temperature for several hours or 37° C. for 1 hour, and diluted 50- to 200-fold with acetonitrile. Absorbance at 278 nm was monitored, and content was determined from linear calibration curves.

Example 2: Sustained Drug Release from Micro-Reservoirs Under Physiological Conditions Micro-reservoirs from Example 1 were tested for sustained release of drug. Micro-reservoir samples of 2 to 5 mg weight were placed in 1.6 ml Eppendorf tubes with 1.2 ml of phosphate buffered saline (PBS) to simulate a physiological environment. After an initial wash to remove any drug not incorporated in the micro-reservoirs, the tubes were incubated at 37° C. with gentle mixing at 250 rpm. The PBS was sampled at time intervals and the released drug quantitated by reverse phase HPLC using a C18 column.

Micro-reservoirs were assayed for drug elution over 5 hours. The resultant drug release was fit to the Korsmeyer-Peppas kinetic equation for drug release from a polymer with dispersed drug. The results of the Korsmeyer-Peppas model are listed in Table 1.

TABLE 1

| Korsmeyer-Peppas Modeling of 5 Hour Drug Release | | | | |
|---|---|---|---|---|
| $Q = a*x^b$ | Microsphere 1 | Microsphere 2 | Microsphere 3 | Microsphere 4 |
| R (correlation coefficient) | 0.9061 | 0.8778 | 0.8579 | 0.9016 |
| SE of estimate | 0.0026 | 0.0025 | 0.0021 | 0.0033 |
| a | 0.0450 | 0.0382 | 0.0305 | 0.0506 |
| b | 0.5241 | 0.5204 | 0.5167 | 0.4502 |

The short term delivery results demonstrate Korsmeyer-Peppas drug release constants typical for drug dispersed in a spherical polymer particle with likely a small contribution from polymer erosion or degradation for Microsphere samples 1, 2, and 3.

Extended drug release study: Microspheres were assayed for drug elution over 7 days using the methods described for testing over 5 hours. The resulting drug release is listed in Table 2.

TABLE 2

| Testing of 7 Day Drug Release | | | | |
|---|---|---|---|---|
| | Cumulative Drug Release, % of Total Drug | | | |
| Time [days] | Microsphere 1 | Microsphere 2 | Microsphere 3 | Microsphere 4 |
| 0 | 0.9% | 1.5% | 2.3% | 2.2% |
| 1 | 1.8% | 2.8% | 3.3% | 3.9% |
| 2 | 2.3% | 4.1% | 4.0% | 5.0% |
| 3 | 4.2% | 6.1% | 4.6% | 5.9% |
| 4 | 5.7% | 13.4% | 5.2% | 6.9% |
| 5 | 7.5% | 19.6% | 5.8% | 7.7% |
| 6 | 10.0% | 26.2% | 6.4% | 8.7% |
| 7 | 11.9% | 30.7% | 7.0% | 9.5% |

The release rates from the 7 day delivery results were fit to the Higuchi equation:

$$Q = A[D(2C - Cs)Cs\, t]^{1/2}$$

$$Q = K_h(t)^{1/2}$$

where Q is the amount of drug released in time t per unit area A, C is the drug initial concentration, Cs is the drug solubility in the polymer media and D is the diffusion coefficient for the drug in the microsphere polymer. In the generalized equation, $K_h$ is the Higuchi constant incorporating the area, diffusion coefficient and drug concentration coefficients.

The Higuchi equation was used to determine the release half-life of the micro-reservoirs and to also to estimate the half-life as a function of the microsphere size. The resultant release half-lives are presented in Table 3.

TABLE 3

Drug Release Half-Life from Higuchi Modeling

| Microsphere Diameter [microns] | $t^{1/2}$ [days] | | | |
| --- | --- | --- | --- | --- |
| | Microsphere 1 | Microsphere 2 | Microsphere 3 | Microsphere 4 |
| 0.5 | 0.14 | 0.02 | 0.42 | 0.11 |
| 1 | 2.29 | 0.34 | 6.65 | 1.70 |
| 1.5 | 11.58 | 1.71 | 33.66 | 8.61 |
| 2 | 36.60 | 5.42 | 106.38 | 27.22 |
| 3 | 185.29 | 27.43 | 538.53 | 137.81 |
| 4 | 585.62 | 86.71 | 1702.01 | 435.55 |
| 5 | 1429.74 | 211.69 | 4155.29 | 1063.36 |
| 6 | 2964.70 | 438.96 | 8616.42 | 2204.98 |
| 7 | 5492.48 | 813.22 | 15962.98 | 4084.99 |
| 8 | 9369.93 | 1387.32 | 27232.13 | 6968.81 |

The results demonstrate that the delivery half-life of drug from the micro-reservoirs may be tailored by the formulation and size of the micro-reservoirs. For a delivery half-life of at least 14 days, a microsphere size of 1.5 micron diameter or greater is estimated to be required.

Verification of extended release: Microsphere Sample 4 was assayed for drug release over 8 weeks using the methods previously described. Due to the relatively long time intervals between sampling as compared to the previous release experiments, the micro-reservoirs may not have released into sink conditions at later time points, potentially slowing effective release rate. The resultant drug release is listed in Table 4.

TABLE 4

Testing of Extended Drug Release Over 56 Days

| Time [days] | Cumulative Eluted Drug [%] |
| --- | --- |
| 0 | 0 |
| 7 | 1.00 |
| 14 | 3.00 |
| 31 | 7.50 |
| 56 | 15.50 |

The results verify sustained release of drug from the micro-reservoirs. Micro-reservoirs may be tailored or selected with a half-life to provide drug through the healing period of the dilated vessel.

Example 3: Formulations of Micro-Reservoirs in Coating Formulation of Cholesterol and Fatty Acid with PEG-Lipid A coating formulation was prepared with 107 mg of stearic acid, 105 mg of cholesterol, and 50 mg of DPPE-mPEG350 mixed with 14 mL of heptane and heated to 60° C. such that a clear solution was obtained. The solution was then vortex mixed for 30 seconds and allowed to cool. Next, 200 mg of sirolimus loaded microspheres of sample #6 was added, and the formulation was placed in an ultrasonic bath for 4 minutes to disperse and suspend the microspheres. [Formulation 1023E]

A coating formulation was prepared with 58 mg of erucic acid, 43 mg of DC-Cholesterol, and 6.25 mg of DOPE-mPEG350 mixed with 7 mL of heptane and heated to 60° C. such that a clear solution was obtained. The solution was then vortex mixed for 30 seconds and allowed to cool. Next, 100 mg of sirolimus loaded microspheres of sample #8 was added, and the formulation was placed in an ultrasonic bath for 5 minutes to disperse and suspend the microspheres. [Formulation 0424A]

A coating formulation was prepared with 25 mg of nervonic acid, 75 mg of DC-Cholesterol, and 6.25 mg of DOPE-mPEG350 mixed with 7 mL of heptane and heated to 60° C. such that a clear solution was obtained. The solution was then vortex mixed for 30 seconds and allowed to cool. Next, 97 mg of sirolimus loaded microspheres of sample #8 was added, and the formulation was placed in an ultrasonic bath for 5 minutes to disperse and suspend the microspheres. [Formulation 0422E]

Example 4: Formulation of Micro-Reservoirs in Coating Formulation of Cholesterol, Fatty Acid, PEG-Lipid and Stabilizing Additive A coating formulation was prepared with 77 mg of stearic acid, 40 mg cholesterol, 50 mg DPPE-mPEG350, and 58 mg of alpha-tocopherol mixed with 7 mL of heptane and heated to 60° C. until a clear solution was obtained. The solution was vortex mixed for 1 minute and allowed to cool to room temperature. Next, 100 mg of sirolimus loaded microspheres of sample #5 was added. The formulation was placed in an ultrasonic bath for 5 minutes to disperse and suspend the microspheres. [Formulation 1009A]

Example 5: Formulation of Micro-Reservoirs in Coating Formulation of Cholesterol and Phospholipid A coating formulation was prepared with 43 mg cholesterol and 42 mg L-alpha-phosphatidylcholine mixed with 7 mL of heptane and heated to 60° C. The solution was vortex mixed for 30 seconds and then allowed to cool to room temperature. Next, 100 mg of sirolimus loaded microspheres from sample #5 were added to the vial which was then placed in an ultrasonic bath for 8 minutes to disperse and suspend the microspheres. [Formulation 0311A]

Example 6: Formulation of Micro-Reservoirs in Coating Formulation of Cholesterol and Long Acyl Chain Phospholipid with and without PEG-Lipid A coating formulation was prepared with 51 mg DC-Cholesterol, 6.25 mg DOPE-mPEG350 and 51 mg dierucoyl phosphatidylcholine (DEPC) mixed with 7 mL of heptane and heated to 60° C. The solution was vortex mixed for 30 seconds and then allowed to cool to room temperature. Next, 100 mg of sirolimus loaded microspheres from sample #7 were added to the vial which was then placed in an ultrasonic bath for 5 minutes to disperse and suspend the microspheres. [Formulation 0410A]

A coating formulation was prepared with 20 mg DC-Cholesterol, 26 mg cholesterol, 6.25 mg DOPE-mPEG350 and 75 mg dinervonyl phosphatidylcholine (DNPC) mixed with 7 mL of heptane and heated to 60° C. The formulation had a weight ratio of DNPC to DC-Cholesterol of 1.6:1. The solution was allowed to cool to room temperature. Next, 97 mg of sirolimus loaded microspheres from sample #7 were added to the vial which was then vortex mixed for 30 seconds and then placed in an ultrasonic bath for 5 minutes to disperse and suspend the microspheres. [Formulation 0421A]

A coating formulation was prepared with 28 mg DC-Cholesterol, 26 mg cholesterol, 6.25 mg DOPE-mPEG350 and 50 mg dinervonyl phosphatidylcholine (DNPC) mixed with 7 mL of heptane and heated to 60° C. The solution was vortex mixed for 30 seconds and then allowed to cool to room temperature. Next, 97 mg of sirolimus loaded microspheres from sample #7 were added to the vial which was then placed in an ultrasonic bath for 5 minutes to disperse and suspend the microspheres. [Formulation 0421B]

A coating formulation was prepared with 50 mg DC-Cholesterol and 50 mg dinervonyl phosphatidylcholine (DNPC) mixed with 7 mL of heptane and heated to 60° C. The formulation had a weight ratio of DNPC to DC-Cholesterol of 1:1. The solution was vortex mixed for 30 seconds and then allowed to cool to room temperature. Next, 100 mg of sirolimus loaded microspheres from sample #7 were added to the vial which was then placed in an ultrasonic bath for 4 minutes to disperse and suspend the microspheres. [Formulation 1205A]

A coating formulation was prepared with 49 mg DC-Cholesterol, 6.25 mg DOPE-mPEG350 and 50 mg dinervonyl phosphatidylcholine (DNPC) mixed with 7 mL of heptane and heated to 60° C. The formulation had a weight ratio of DNPC to DC-Cholesterol of 1:1. The solution was vortex mixed for 30 seconds and then allowed to cool to room temperature. Next, 100 mg of sirolimus loaded microspheres from sample #7 were added to the vial which was then placed in an ultrasonic bath for 2 minutes to disperse and suspend the microspheres. [Formulation 1209A]

A coating formulation was prepared with 76 mg DC-Cholesterol, 6.25 mg DOPE-mPEG350 and 25 mg dinervonyl phosphatidylcholine (DNPC) mixed with 7 mL of heptane and heated to 60° C. The formulation had a weight ratio of DNPC to DC-Cholesterol of 1:3. The solution was allowed to cool to room temperature. Next, 100.7 mg of sirolimus loaded microspheres from sample #8 were added to the vial, vortex mixed for 30 seconds and then placed in an ultrasonic bath for 5 minutes to disperse and suspend the microspheres. [Formulation 0513A]

Example 7: Formulation of Micro-Reservoirs in Coating Formulation of DC-Cholesterol with Varying PEG-Lipid Content A coating formulation was prepared with 12.5 mg of DOPE-mPEG350, 44 mg of DC-Cholesterol and 44 mg of dinervonoyl phosphatidylcholine (DNPC) mixed with 7 mL of heptane heated to 60° C. The clear solution was allowed to cool to room temperature, then 97 mg of sirolimus loaded microspheres from microsphere from sample #8 were added. The formulation was then placed in an ultrasonic bath and sonicated for 5 minutes to disperse and suspend the microspheres. [Formulation 0422A]

A coating formulation was prepared with 25 mg of DOPE-mPEG350, 37.5 mg of DC-Cholesterol and 37.5 mg of dinervonoyl phosphatidylcholine (DNPC) mixed with 7 mL of heptane heated to 60° C. The clear solution was allowed to cool to room temperature then 97 mg of sirolimus loaded microspheres from microsphere sample #8 were added. The formulation was then placed in an ultrasonic bath and sonicated for 5 minutes to disperse and suspend the microspheres. [Formulation 0422B]

Example 8: Coating with Additional Drug

A coating formulation was prepared with 72.9 mg DC-cholesterol in 7 mL of heptane and heated to 60 C until the DC-cholesterol was solubilized to produce a clear solution. To the solution was added 15.5 mg of sirolimus and vortex mixed for 30 seconds. The solution was heated for 40 minutes, vortexing 10 seconds every 10 minutes and sonicated for 5 minutes while cooling to room temperature. To the solution was added 50 mg of DNPC. When at room temperature, the solution was filtered through a 0.2 micron PTFE filter to remove large drug particles. The solution was left overnight with no observed particulates formed overnight. The solution was assayed, and the sirolimus content was found to be 0.96 mg per ml. To the solution was added 98 mg of sirolimus loaded microspheres from microsphere sample #8, vortex mixed for 30 seconds and sonicated for 8 minutes to disperse and suspend the microspheres. The resulting coating formulation contained 0.71% by weight sirolimus of which 19.1% of the drug was in the DC-cholesterol and DNPC hydrophobic matrix with the remainder in the microspheres. [Formulation 0512A]

The weight percentage compositions of the coating formulations described in Examples 3, 4, 5, 6, 7 and 8 are presented in Table 5.

TABLE 5

Weight percentage compositions of coating formulations

| Coating Formulation | Fatty Acid or Phospholipid [%] | Cholesterol [%] | PEG-Lipid [%] | Microspheres [%] | Other [%] | Heptane [%] | Sirolimus [%] |
|---|---|---|---|---|---|---|---|
| 1023E | Stearic Acid 1.07% | Cholesterol 1.05% | DPPE-mPEG350 0.50% | 2.01% | | 95.37% | 0.58% |
| 0424A | Erucic Acid 1.17% | DC Cholesterol 0.87% | DOPE-mPEG350 0.13% | 2.01% | | 95.82% | 0.59% |
| 0422E | Nervonic Acid 0.50% | DC Cholesterol 1.51% | DOPE-mPEG350 0.13% | 1.96% | | 95.90% | 0.57% |
| 1009A | Stearic Acid 1.52% | Cholesterol 0.79% | DPPE-mPEG350 0.98% | 1.97% | alpha Tocopherol 1.14% | 93.60% | 0.45% |
| 0311A | L-alpha Phosphatidylcholine 0.85% | Cholesterol 0.87% | | 2.02% | | 96.26% | 0.47% |
| 0410A | DEPC 1.03% | DC Cholesterol 1.03% | DOPE-mPEG350 0.13% | 2.01% | | 95.81% | 0.56% |

TABLE 5-continued

Weight percentage compositions of coating formulations

| Coating Formulation | Fatty Acid or Phospholipid [%] | Cholesterol [%] | PEG-Lipid [%] | Microspheres [%] | Other [%] | Heptane [%] | Sirolimus [%] |
|---|---|---|---|---|---|---|---|
| 0421A | DNPC 1.51% | Cholesterol/DC Cholesterol 0.52%/0.40% | DOPE-mPEG350 0.13% | 1.95% | | 95.50% | 0.54% |
| 0421B | DNPC 1.01% | Cholesterol/DC Cholesterol 0.52%/0.56% | DOPE-mPEG350 0.13% | 1.95% | | 95.82% | 0.54% |
| 1205A | DNPC 1.01% | DC Cholesterol 1.01% | | 2.02% | | 95.96% | 0.56% |
| 1209A | DNPC 1.01% | DC Cholesterol 0.99% | DOPE-mPEG350 0.13% | 2.02% | | 95.86% | 0.56% |
| 0513A | DNPC 0.50% | DC Cholesterol 1.53% | DOPE-mPEG350 0.13% | 2.03% | | 95.81% | 0.60% |
| 0422A | DNPC 0.89% | DC Cholesterol 0.89% | DOPE-mPEG350 0.25% | 1.96% | | 96.01% | 0.58% |
| 0422B | DNPC 0.76% | DC Cholesterol 0.76% | DOPE-mPEG350 0.50% | 1.96% | | 96.02% | 0.58% |
| 0512A | DNPC 1.00% | DC Cholesterol 1.46% | | 1.97% | Sirolimus in Hydrophobic Matrix 0.13% | 95.43% | 0.71% |

Example 9: Application of Coating Formulation to Balloon Catheter

The stearic acid coating formulation of Example 3 (Formulation 1023E) was sprayed onto the balloon surface of 5.0 mm diameter×20 mm length Nylon angioplasty balloons. Seven ml of the coating formulation was loaded into a 25 mL gas-tight syringe with an integrated magnetic stir bar system. The formulation was continuously stirred during spraying to keep the drug micro-reservoirs well suspended. A syringe pump delivered the coating formulation at a rate of 0.11 mL/min through a 120 kHz ultrasonic nozzle being activated with 5.5 watts of power [Sonotek DES1000]. To verify process parameters, a 5.0 mm diameter×20 mm length cylinder of balloon material was cut, weighed and placed over the same size balloon. This sleeve of balloon material was then coated and weighed to verify approximately 2.2 mg total coating was applied, corresponding to 7 µg/mm² of coating density. Of this 7 µg/mm² of the formulation from Example 3, stearic acid comprised approximately 1.6 µg/mm², cholesterol comprised 1.6 µg/mm², DPPE-mPEG350 0.8 µg/mm² and sirolimus loaded microspheres from microsphere sample #5 at 3 µg/mm² resulting in a drug density of 0.87 µg/mm². Once sleeve weights confirmed target weight had been reached, full balloons were coated. A 5.0 mm diameter×20 mm length balloon was inflated, positioned underneath the spray and then rotated constantly while moving back and forth 5 times. The balloon was then removed and allowed to dry. The process was repeated until 6 balloons were coated. This same process was repeated to spray the coating formulation of Example 6 (Formulation 0513A) on 3.0 mm diameter×20 mm length balloons. The sleeve coating target weight for a 3.0 mm diameter×20 mm length balloon with the formulation of Example 6 (Formulation 0513A) was 1.4 mg to achieve a coating density of 7.6 µg/mm². Of this 7.6 µg/mm², dinervonoyl phosphatidylcholine comprised 0.9 µg/mm², DC-cholesterol 2.7 µg/mm², DOPE-mPEG350 0.23 µg/mm², and the sirolimus loaded microspheres of sample #5 comprised 3.7 µg/mm² resulting in a drug density of 1.08 µg/mm².

The coating formulations of Examples 4, 5, 6, 7 and 8 were also sprayed onto the surface of 20 mm length balloons in the manner of spraying the formulation of Example 3 previously described. The resultant coating weights and coating densities are presented in Table 6.

TABLE 6

Coating of Balloon Catheters

| Example | Formulation | Balloon Diameter [mm] | Coating Formulation % Solids (w/w) [%] | Coating Weight [mg] | Coating Density [ug/mm²] | Cholesterol Density [ug/mm²] | Fatty Acid or Phospholipid Density [ug/mm²] | PEG-lipid Density [ug/mm²] | Microsphere Density [ug/mm²] | Drug Density [ug/mm²] |
|---|---|---|---|---|---|---|---|---|---|---|
| 3 | 1023E | 5 | 4.86% | 2.19 | 6.97 | 1.58 | 1.61 | 0.75 | 3.02 | 0.87 |
| 3 | 424A | 5 | 4.36% | 2.05 | 6.53 | 1.35 | 1.83 | 0.20 | 3.15 | 0.93 |
| 3 | 0422E | 5 | 4.27% | 1.82 | 5.79 | 2.14 | 0.71 | 0.18 | 2.76 | 0.81 |
| 4 | 109A/1010D | 5 | 6.83% | 2.54 | 8.09 | 1.00 | 1.92 | 1.24 | 2.49 | 0.57 |
| 5 | 0311A | 5 | 3.89% | 1.7 | 5.41 | 1.26 | 1.23 | 0.00 | 2.93 | 0.67 |

TABLE 6-continued

Coating of Balloon Catheters

| Example | Formulation | Balloon Diameter [mm] | Coating Formulation % Solids (w/w) [%] | Coating Weight [mg] | Coating Density [ug/mm$^2$] | Cholesterol Density [ug/mm$^2$] | Fatty Acid or Phospholipid Density [ug/mm$^2$] | PEG-lipid Density [ug/mm$^2$] | Microsphere Density [ug/mm$^2$] | Drug Density [ug/mm$^2$] |
|---|---|---|---|---|---|---|---|---|---|---|
| 6 | 410A | 5 | 4.38% | 2.31 | 7.35 | 1.80 | 1.80 | 0.22 | 3.53 | 0.98 |
| 6 | 0421A | 5 | 4.71% | 1.88 | 5.98 | 1.23 | 2.00 | 0.17 | 2.59 | 0.72 |
| 6 | 0421B | 5 | 4.36% | 1.83 | 5.83 | 1.52 | 1.41 | 0.18 | 2.73 | 0.76 |
| 6 | 1205A | 5 | 4.20% | 1.78 | 5.67 | 1.42 | 1.42 | 0.00 | 2.83 | 0.78 |
| 6 | 1209A | 5 | 4.32% | 2.24 | 7.13 | 1.70 | 1.74 | 0.22 | 3.47 | 0.96 |
| 6 | 513A | 3 | 4.37% | 1.43 | 7.59 | 2.77 | 0.91 | 0.23 | 3.67 | 1.08 |
| 7 | 0422A | 5 | 4.15% | 1.8 | 5.73 | 1.28 | 1.28 | 0.36 | 2.81 | 0.83 |
| 7 | 0422B | 5 | 4.14% | 1.83 | 5.83 | 1.11 | 1.11 | 0.74 | 2.87 | 0.84 |
| 8 | 512A | 3 | 4.79% | 1.51 | 8.01 | 2.57 | 1.76 | 0.00 | 3.45 | 1.25 |

For the balloons coated with the formulation of Example 4, each balloon was sprayed with an additional top coat formulation (1010D) consisting of 1 mg of cholesterol and cholesterol-PEG600 coating to cover the micro-reservoir layer. To make this top coating, 23 mg of cholesterol-PEG600 and 224 mg of cholesterol were dissolved in 7 mL of isopropanol. The target coating weight of 1 mg on a 5.0 mm diameter×20 mm long balloon corresponds to 3.2 µg/mm$^2$ of total top coating comprised of 0.3 µg/mm$^2$ cholesterol-PEG600 and 2.9 µg/mm$^2$ cholesterol.

Example 10: Adhesion of Coatings to Vessel Luminal Surface

Ex-vivo porcine arteries were flushed with 37° C. Lactated Ringer's solution at 50 mL/min pulsatile flow (approximately 72 BPM) for 5 minutes. The balloons coated with the formulation of Example 3 were inflated in the lumen of ex-vivo porcine arteries to an approximate overstretch of 1:1.2 to transfer the drug containing coating to the vessel lumen. The solution that passed through the arteries prior to and after inflation (pre and post flush), the balloon used for the arteries, and the section of artery contacting the inflated balloon were subsequently assayed for drug after 5 minutes of post inflation flush. The vessels treated with formulations 1205A and 1209A were flushed for a total of 60 minutes to evaluate extended stability of the transferred coating. The amount of drug measured from all sources in the assay was totaled and compared to the estimated drug content of the balloon based on coating weight. The proportion of drug transferred to the artery based on the estimated drug content of the balloon by coating weight was used as a measure of transfer efficiency.

TABLE 7

Stearic Acid - Cholesterol Formulation [Formulation 1023E]

| Balloon Sample | Sirolimus Recovered [ug] | | | | | % of Total | |
|---|---|---|---|---|---|---|---|
| | 1 min Pre Flush | 1 min Post Flush | 2 min Post Flush | Balloon Residual | Artery | Total Sirolimus Recovered [µg] | Sirolimus on Balloon Transferred to Artery |
| 53 | 12 | 110 | 10 | 9 | 66 | 207 | 16 |
| 54 | 27 | 120 | 10 | 19 | 90 | 266 | 22 |
| 55 | 30 | 87 | 7 | 26 | 136 | 286 | 33 |
| 56 | 23 | 177 | 10 | 6 | 53 | 269 | 13 |
| 57 | 37 | 186 | 9 | 6 | 99 | 337 | 24 |
| 58 | 16 | 148 | 10 | 0 | 38 | 212 | 9 |
| Average | 24.2 | 138.0 | 9.3 | 11.0 | 80.3 | 262.8 | 19.5 |
| SD | 9.2 | 39.17 | 1.2 | 9.6 | 35.5 | 48.6 | 9 |

TABLE 8

Erucic Acid - DC-Cholesterol Formulation [Formulation 0424A]

| Balloon Sample | Sirolimus Recovered [ug] | | | | | Total | % of Total |
|---|---|---|---|---|---|---|---|
| | 1 min Pre Flush | 1 min Post Flush | 2 min Post Flush | Balloon Residual | Artery | Sirolimus Recovered [µg] | Sirolimus on Balloon Transferred to Artery |
| 0424A-1 | 1 | 4 | 1 | 160 | 8 | 185 | 3 |
| 0424A-2 | 2 | 5 | 2 | 214 | 12 | 247 | 5 |
| 0424A-3 | 2 | 9 | 1 | 253 | 7 | 290 | 3 |
| Average | 1.8 | 5.9 | 1.5 | 209.2 | 8.8 | 240.8 | 3.9 |
| SD | 0.4 | 2.7 | 0.8 | 46.7 | 2.9 | 53.0 | 1.3 |

TABLE 9

Nervonic Acid - DC-Cholesterol Formulation [Formulation 0422E]

| Balloon Sample | Sirolimus Recovered [µg] | | | | | Total Sirolimus Recovered [µg] | % of Total Sirolimus on Balloon Transferred to Artery |
|---|---|---|---|---|---|---|---|
| | 1 min Pre Flush | 1 min Post Flush | 2 min Post Flush | Balloon Residual | Artery | | |
| 0422E-1 | 5 | 28 | 6 | 128 | 62 | 229 | 22 |
| 0422E-2 | 3 | 39 | 4 | 90 | 35 | 171 | 12 |
| 0422E-3 | 16 | 8 | 4 | 76 | 84 | 187 | 29 |
| Average | 8 | 25 | 4 | 98 | 61 | 196 | 21.2 |
| SD | 7 | 16 | 1 | 27 | 25 | 30 | 8.6 |

The balloons coated with the formulation of Example 4 were also tested in ex-vivo porcine arteries.

TABLE 10

Stearic Acid - Cholesterol-alpha Tocopherol Formulation [Formulation 1009A/1010D]

| Balloon Sample | Sirolimus Recovered [µg] | | | | | Total Sirolimus Recovered [µg] | % of Total Sirolimus on Balloon Transferred to Artery |
|---|---|---|---|---|---|---|---|
| | 1 min Pre Flush | 1 min Post Flush | 2 min Post Flush | Balloon Residual | Artery | | |
| 40 | N/A | 78 | 3 | 354 | 28 | 463 | 6 |
| 41 | 12 | 120 | 4 | 301 | 31 | 468 | 6 |

The balloons coated with the formulation of Example 5 were also tested in ex-vivo porcine arteries.

TABLE 11

L-alpha-Phosphatidylcholine - Cholesterol Formulation [Formulation 0311A]

| Balloon Sample | Sirolimus Recovered [µg] | | | | | Total Sirolimus Recovered [µg] | % of Total Sirolimus on Balloon Transferred to Artery |
|---|---|---|---|---|---|---|---|
| | 1 min Pre Flush | 1 min post | 2 min post | Balloon residual | Artery | | |
| 0311A-1 | 51 | 60 | 4 | 12 | 26 | 153 | 9 |
| 0311A-2 | 100 | 74 | 4 | 25 | 7 | 210 | 2 |
| 0311A-3 | 44 | 92 | 5 | 26 | 45 | 212 | 15 |
| Average | 65.0 | 75.3 | 4.3 | 21.0 | 26.0 | 191.7 | 8.7 |
| SD | 30.5 | 16.0 | 0.6 | 7.8 | 19.0 | 33.5 | 6.5 |

The balloons coated with the formulation of Example 6 were also tested in ex-vivo porcine arteries.

TABLE 12

DEPC - DC-Cholesterol [Formulation 0410A]

| Balloon Sample | Sirolimus Recovered [µg] | | | | | Total Sirolimus Recovered [µg] | % of Total Sirolimus on Balloon Transferred to Artery |
|---|---|---|---|---|---|---|---|
| | 1 min Pre Flush | 1 min post | 2 min post | Balloon residual | Artery | | |
| 0410A-1 | 17 | 21 | 3 | 12 | 196 | 249 | 52 |
| 0410A-2 | 34 | 12 | 2 | 15 | 228 | 290 | 60 |
| 0410A-3 | 17 | 30 | 1 | 14 | 137 | 199 | 53 |
| Average | 65 | 75 | 4 | 21 | 26 | 192 | 55 |
| SD | 31 | 16 | 1 | 8 | 19 | 34 | 6.3 |

TABLE 13

DNPC - DC-Cholesterol Formulation [Formulation 0421A]

| Balloon Sample | Sirolimus Recovered [µg] | | | | | Total Sirolimus Recovered [µg] | % of Total Sirolimus on Balloon Transferred to Artery |
|---|---|---|---|---|---|---|---|
| | 1 min Pre Flush | 1 min post | 2 min post | Balloon residual | Artery | | |
| 0421A-1 | 16 | 6 | 1 | 32 | 127 | 259 | 40% |
| 0421A-2 | 18 | 13 | 3 | 29 | 114 | 240 | 35% |
| 0421A-3 | 21 | 9 | 7 | 24 | 138 | 264 | 43% |
| Average | 18.4 | 9.4 | 3.6 | 28.4 | 126.4 | 254.4 | 39.4% |
| SD | 2.7 | 3.6 | 2.7 | 4.2 | 12.2 | 12.5 | 3.8% |

TABLE 14

DNPC - DC-Cholesterol - Cholesterol Formulation [Formulation 0421B]

| Balloon Sample | Sirolimus Recovered [µg] | | | | | Total Sirolimus Recovered [µg] | % of Total Sirolimus on Balloon Transferred to Artery |
|---|---|---|---|---|---|---|---|
| | 1 min Pre Flush | 1 min post | 2 min post | Balloon residual | Artery | | |
| 0421B-1 | 8 | 16 | 1 | 120 | 131 | 276 | 45 |
| 0421B-2 | 5 | 21 | 2 | 196 | 108 | 331 | 37 |
| 0421B-3 | 4 | 22 | 5 | 137 | 83 | 250 | 28 |
| Average | 5.3 | 19.7 | 2.7 | 151.2 | 107.1 | 286.0 | 36.7 |
| SD | 2.1 | 2.9 | 2.0 | 39.9 | 23.9 | 41.3 | 8.2 |

TABLE 15

DNPC - DC-Cholesterol (no PEG-Lipid) Formulation [Formulation 1205A]

| Balloon Sample | Sirolimus Recovered [µg] | | | | | Total Sirolimus Recovered [µg] | % of Total Sirolimus on Balloon Transferred to Artery |
|---|---|---|---|---|---|---|---|
| | 1 min Pre Flush | 1 min post | 2 min post | Balloon residual | Artery | | |
| 106 | 14 | 47 | 3 | 94 | 168 | 326 | 47 |
| 105 | 10 | 84 | 5 | 142 | 165 | 406 | 46 |
| 107 | 8 | 68 | 4 | 100 | 147 | 327 | 41 |
| 108 | 9 | 43 | 4 | 121 | 144 | 321 | 41 |
| 109 | 4 | 66 | 9 | 62 | 158 | 299 | 45 |
| 110 | 3 | 52 | 1 | 128 | 126 | 310 | 35 |
| Average | 8.0 | 60.0 | 4.3 | 107.8 | 151.3 | 331.5 | 42.5 |
| SD | 4.0 | 15.5 | 2.7 | 28.6 | 15.6 | 38.0 | 4.5 |

TABLE 16

[DNPC - DC-Cholesterol (PEG-Lipid) Formulation [Formulation 1209A]

| Balloon Sample | Sirolimus Recovered [µg] | | | | | Total Sirolimus Recovered [µg] | % of Total Sirolimus on Balloon Transferred to Artery |
|---|---|---|---|---|---|---|---|
| | 1 min Pre Flush | 1 min post | 2 min post | Balloon residual | Artery | | |
| 124 | 5 | 64 | 1 | 30 | 148 | 248 | 38 |
| 125 | 5 | 79 | 4 | 88 | 158 | 334 | 41 |
| 126 | 4 | 45 | 9 | 144 | 152 | 354 | 39 |
| 127 | 8 | 73 | 5 | 135 | 124 | 345 | 32 |
| 128 | 2 | 49 | 5 | 98 | 190 | 344 | 49 |
| 129 | 4 | 89 | 5 | 90 | 149 | 337 | 38 |
| Average | 4.7 | 66.5 | 4.8 | 97.5 | 153.5 | 327.0 | 39.5 |
| SD | 2.0 | 17.2 | 2.6 | 40.7 | 21.3 | 39.3 | 5.5 |

TABLE 17

DNPC - DC-Cholesterol (PEG-Lipid) Formulation [Formulation 0513A]

| Balloon Sample | Sirolimus Recovered [µg] | | | | | Total Sirolimus Recovered [µg] | % of Total Sirolimus on Balloon Transferred to Artery |
|---|---|---|---|---|---|---|---|
| | 1 min Pre Flush | 1 min post | 2 min post | Balloon residual | Artery | | |
| 0513A-1 | 6 | 4 | 1 | 134 | 67 | 212 | 30% |
| 0513A-2 | 5 | 12 | 2 | 150 | 85 | 254 | 38% |
| 0513A-3 | 5 | 2 | 1 | 152 | 88 | 248 | 39% |
| Average | 5.3 | 6.0 | 1.3 | 145.3 | 80.0 | 238.0 | 35.4% |
| SD | 0.6 | 5.3 | 0.6 | 9.9 | 11.4 | 22.7 | 5.0% |

Figure 4:
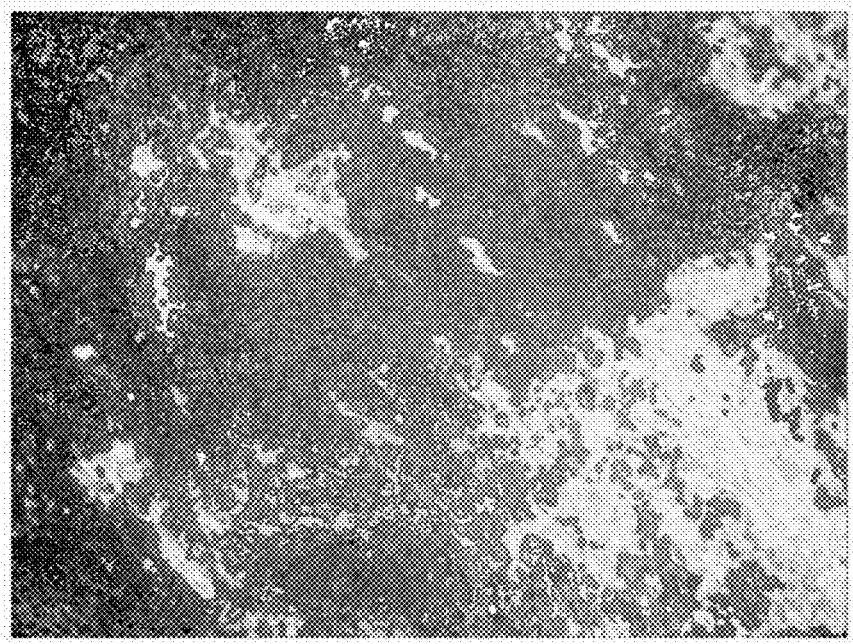
FIG. 4 is a photomicrograph of the luminal surface of a vessel treated with one embodiment of the balloon catheter.
Figure 5:
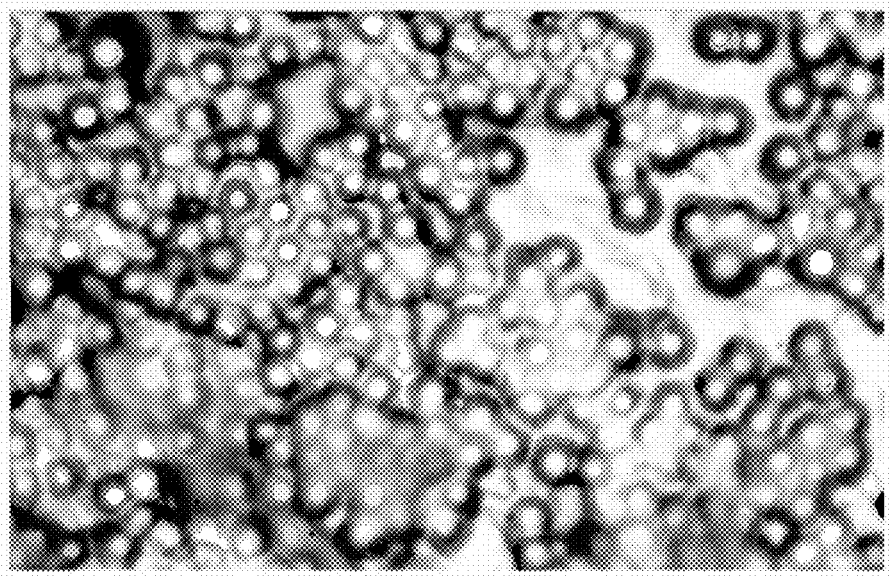
FIG. 5 is a photomicrograph of the luminal surface of a vessel treated with one embodiment of the balloon catheter.

The luminal surface of the artery after inflation of the balloon coated with Formulation 1209A and after one hour of post inflation fluid flush was viewed under darkfield microscopy. FIG. 4 is a photomicrograph of the luminal surface at 200× magnification showing adhered material. FIG. 5 is a photomicrograph of the surface at 1000× magnification showing the adhered material to be a layer of spherical micro-reservoirs surrounded by coating material.

Example 11: Adhesion of Coatings to Vessel Luminal Surface of Formulations with Varying PEG-Lipid Content The samples from Example 7 were tested for coating transfer and resistance to wash-off using the methods of Example 10. The results have been tabulated to compare the coatings with DNPC and DC-Cholesterol in equal weight proportion with varying amounts of DOPE-mPEG350. [Formulations 1205A, 1209A, 0422A, 0422B]

TABLE 18

Coating Transfer and Resistance to Wash-Off for Various Coating Formulations

| Formulation | Sirolimus Recovered [µg] | | | | | Total Sirolimus Recovered [µg] | % of Total Sirolimus on Balloon Transferred to Artery |
|---|---|---|---|---|---|---|---|
| | 1 min Pre Flush | 1 min post | 2 min post | Balloon residual | Artery | | |
| No PEG-lipid | 8.0 ± 4.0 | 60.0 ± 15.5 | 4.3 ± 2.7 | 107.8 ± 28.6 | 151.3 ± 15.6 | 331.5 ± 38.0 | 42.5 ± 4.5 |
| 5.9% mPEG 350 | 4.7 ± 2.0 | 66.5 ± 17.2 | 4.8 ± 2.6 | 97.5 ± 40.7 | 153.5 ± 21.3 | 327.0 ± 39.3 | 39.5 ± 5.5 |
| 12.4% mPEG 350 | 6.5 ± 3.2 | 38.9 ± 21.0 | 4.5 ± 0.6 | 107.4 ± 35.5 | 90.4 ± 29.2 | 247.6 ± 55.1 | 30.0 ± 9.7% |
| 25% mPEG 350 | 25.0 ± 26.1 | 68.3 ± 36.7 | 6.2 ± 3.2 | 17.9 ± 12.0 | 106.7 ± 19.8 | 224.1 ± 27.8 | 36.0 ± 6.7% |

The results demonstrate significant transfer of drug coating to the vessel lumen. Drug coating loss during pre-flush was increased for coating formulation with 25% PEG-lipid.

Example 12: Adhesion of Coating with Additional Rapamycin to Vessel Luminal Surface The formulation of Example 8 was tested for coating transfer and resistance to wash-off using the methods of Example 10.

TABLE 19

DNPC - DC-Cholesterol Formulation with Additional Drug [Formulation 0512A]

| Balloon Sample | Sirolimus Recovered [μg] | | | | | Total Sirolimus Recovered [μg] | % of Total Sirolimus on Balloon Transferred to Artery |
|---|---|---|---|---|---|---|---|
| | 1 min Pre Flush | 1 min post | 2 min post | Balloon residual | Artery | | |
| 0512A-1 | 3 | 43 | 2 | 155 | 76 | 279 | 29% |
| 0512A-2 | 5 | 9 | 10 | 51 | 39 | 114 | 15% |
| 0512A-3 | 6 | 8 | 2 | 135 | 47 | 198 | 18% |
| Average | 4.7 | 20.0 | 4.7 | 113.7 | 54.0 | 197.0 | 20.9% |
| SD | 1.5 | 19.9 | 4.6 | 55.2 | 19.5 | 82.5 | 7.5% |

The results demonstrate significant transfer of drug to the vessel lumen from a coating with additional drug added to the phospholipid and cholesterol components of the coating formulation.

Example 13: Drug Release into Treated Vessel In-Vivo

To prepare balloon catheters coated with drug micro-reservoir containing formulation, 100 mg of DNPC, 103 mg DC-Cholesterol and 12.5 mg DOPE-mPEG350 was mixed into 14 mL of heptane. The mixture was heated to 60° C. to dissolve the solid components and cooled to room temperature. Next, 195 mg of microsphere sample #6 were added and stirred to suspend the microspheres. Balloon catheters with balloons of 3.0 mm diameter×20 mm length were coated with the formulation using the methods described in Example 9. The coated balloon catheters were allowed to dry. An average of 1.28 mg±0.12 mg of dried coating was applied to the balloons, resulting in a coating density of 6.80 μg/mm$^2$ and a drug density of 1.06 μg/mm$^2$. The balloons were deflated and folded to a pre-deployment configuration with a smaller cross-section and packaged in a sleeve to retain the folded configuration. The balloon catheters were packaged and sterilized by ionizing radiation at a dose of 25 kiloGray minimum.

The iliofemoral artery of rabbits was used to assess the in-vivo transfer of the drug coating to an arterial vessel. The iliofermoral artery segment for treatment was first denuded of endothelium to reproduce post-angioplasty tissue damage. A dissection was made to the common carotid artery, and a size 5F balloon wedge catheter was inserted into the artery and directed under fluoroscopic guidance to the treatment site of the iliofemoral artery. Contrast agent was injected through the catheter and angiograms of the iliofemoral arteries recorded. The balloon wedge catheter was exchanged for a 3.0 mm diameter×8 mm length standard angioplasty balloon catheter under fluoroscopic guidance, inflated, and withdrawn proximally in its inflated state approximately to the level of the iliac bifurcation to denude the section of the artery. The angioplasty balloon catheter was exchanged for a drug coated balloon catheter. The catheter was advanced to the denuded vessel segment and inflated for 120 seconds. The balloon was deflated and withdrawn. Both the right and left iliac arteries of each animal were treated.

A total of eleven animals were treated. One animal (2 iliac arteries treated) was euthanized 1 hour after treatment and vessel segments recovered for microscopic examination. Another animal (2 iliac arteries treated) was euthanized 24 hours after treatment and vessel segments recovered for microscopic examination. Three animals (6 iliac arteries) were recovered at each time point of 1 hour, 7 days and 28 days. Blood samples were taken from these animals prior to surgery, at 0.5, 1, 4 hours post treatment and at sacrifice. The vessel segments were recovered and assayed for drug content by HPLC/MS quantitation.

Assay of the blood samples showed a rapid decline of drug in circulating blood with a concentration of 4.75 ng/ml at 30 minutes, 2.63 ng/ml at 1 hour and 0.82 ng/ml at 4 hours. The blood concentration of drug collected at sacrifice for the 7 day and 28 day time points were below the limit of detection for the quantitation assay. The blood levels were fit to an exponential decay curve with a half-life of 0.77 hours, indicating rapid dilution and clearance of drug from the bloodstream Scanning electron microscopy and light microscopy of the tissue samples collected 1 hour and 24 hours after treatment showed a layer of material on the vessel lumen surface with spherical drug micro-reservoirs observed within the layer. Patchy areas of fibrin were observed on the luminal surface but no large fibrin deposits indicative of blood incompatibility were observed to be associated with the coating.

Assay of the treated vessel segments demonstrated tissue drug levels of 261 μg/g±116.5 μg/g at 1 hour after treatment, 43.8 μg/g±34.2 μg/g at 7 days after treatment and 21.5 μg/g±17.3 μg/g at 28 days after treatment. The results indicate adhesion of the drug containing micro-reservoir coating to the luminal surface of an artery with sustained presence of drug associated with the tissues of the treated vessel through 28 days. The tissue associated levels of drug demonstrated a rapid initial decline which slowed between 7 to 28 days. The tissue associated drug levels from 7 and 28 days were fit to an exponential decay, indicating a half-life of approximately 20.4 days.

Additional Embodiments

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, it is contemplated that various aspects and features of the invention described can be practiced separately, combined together, or substituted for one another, and that a variety of combination and sub-combinations of the features and aspects can be made and still fall within the scope of the invention. Further, the disclosure herein of any particular feature, aspect, method, property, characteristic, quality, attribute, element, or the like in connection with an embodiment can be used in all other embodiments set forth herein. Thus, it is intended that the scope of the present invention herein disclosed should not be limited by the particular disclosed embodiments described above, but should be determined only by a fair reading of the claims.

Conditional language, such as, among others, "could," "might," or "may," unless specifically stated otherwise, or otherwise understood within the context as used, is generally intended to convey that certain embodiments include while other embodiments do not include, certain features or elements. Thus, such conditional language is not generally intended to imply that features or elements are in any way required for one or more embodiments.

Summary of Embodiments

A coating for an expandable portion of a catheter comprising a hydrophobic matrix and a dispersed phase comprising a plurality of micro-reservoirs dispersed in the hydrophobic matrix, wherein the plurality of micro-reservoirs comprises a first active agent and a first biodegradable or bioerodable polymer.

In embodiments of the coating as described above, the first active agent is intermixed with or dispersed in the first biodegradable or bioerodable polymer.

In embodiments of the coating as described above, the plurality of micro-reservoirs further comprises a second active agent. The second active agent is selected from the group consisting of paclitaxel, sirolimus, paclitaxel derivative, sirolimus derivative, paclitaxel analogues, sirolimus analogues, inhibitory RNA, inhibitory DNA, steroids, and complement inhibitors.

In embodiments of the coating as described above, the plurality of micro-reservoirs further comprises a second biodegradable or bioerodable polymer. The second biodegradable or bioerodable polymer is selected from the group consisting of polylactic acid, polyglycolic acid and their copolymers, polydioxanone, polycaprolactone, polyphosphazine, collagen, gelatin, chitosan, glycosoaminoglycans, and combination thereof.

In embodiments of the coating as described above, the hydrophobic matrix comprises at least one hydrophobic compound selected from the group consisting of sterols, lipids, phospholipids, fats, fatty acids, surfactants, and their derivatives.

In some embodiments of the coating described above, wherein the hydrophobic matrix comprises a cholesterol and a fatty acid. In some embodiments, the weight ratio of cholesterol to fatty acid is in the range of about 1:2 to about 3:1.

In embodiments of the coating as described above, the fatty acid is selected from the group consisting of lauric acid, lauroleic acid, tetradeadienoic acid, octanoic acid, myristic acid, myristoleic acid, decenoic acid, decanoic acid, hexadecenoic acid, palmitoleic acid, palmitic acid, linolenic acid, linoleic acid, oleic acid, vaccenic acid, stearic acid, eicosapentaenoic acid, arachadonic acid, mead acid, arachidic acid, docosahexaenoic acid, docosapentaenoic acid, docosatetraenoic acid, docosenoic acid, tetracosanoic acid, hexacosenoic acid, pristanic acid, phytanic acid, and nervonic acid.

In other embodiments of the coating described above, wherein the hydrophobic matrix comprises a cholesterol and a phospholipid. In some embodiments, the weight ratio of cholesterol to phospholipid is in the range of about 1:2 to about 3:1.

In some embodiments, the phospholipid is selected from the group consisting of phosphatidylcholine, phosphatidylethanolamine, phosphatidylserine, and phosphatidylinositol.

In some embodiments, the phospholipid is a cationic phospholipid. In some embodiments, the cationic phospholipid is phosphatidylethanolamine, dioleoylphosphatidylethanolamine (DOPE), or an amine derivative of phosphatidylcholine.

In some embodiments, the phospholipid comprises an acyl chain length of about 20 to about 34 carbons. In some embodiments, the phospholipid is selected from the group consisting of dieicosenoyl phosphatidylcholine (1,2-dieicosenoyl-sn-glycero-3-phosphocholine, C20:1 PC), diarachidonoyl phosphatidylcholine (1,2-diarachidoyl-sn-glycero-3-phosphocholine, C20:0 PC), dierucoyl phosphatidylcholine (1,2-dierucoyl-sn-glycero-3-phosphocholine, C22:1 PC), didocosahexaenoyl phosphatidylcholine (1,2-didocosahexaenoyl-sn-glycero-3-phosphocholine, C22:6 PC), heneicosenoyl phosphatidylcholine (1,2-heneicosenoyl-sn-glycero-3-phosphocholine, C21:1 PC) and dinervonyl phosphatidylcholine (1,2-dinervonoyl-sn-glycero-3-phosphocholine, C24:1 PC).

In embodiments of the coating as described above, the cholesterol is DC-Cholesterol.

In embodiments of the coating as described above, the plurality of micro-reservoirs is about 10% to about 75% by weight of the coating.

In embodiments of the coating as described above, the plurality of micro-reservoirs has an average diameter of about 1.5 microns to about 8 microns. In some embodiments, the plurality of micro-reservoirs has an average diameter of about 2 microns to about 6 microns. In some embodiments, the plurality of micro-reservoirs has an average diameter of about 3 microns to about 5 microns.

In embodiments of the coating as described above, the plurality of micro-reservoirs has an active ingredient release kinetics with a half-life of at least 14 days.

In embodiments of the coating as described above, the first biodegradable or bioerodable polymer is selected from the group consisting of polylactic acid, polyglycolic acid and their copolymers, polydioxanone, polycaprolactone, polyphosphazine, collagen, gelatin, chitosan, glycosoaminoglycans, and combination thereof.

In embodiments of the coating as described above, the first active agent is selected from the group consisting of paclitaxel, sirolimus, paclitaxel derivative, sirolimus derivative, paclitaxel analogues, sirolimus analogues, inhibitory RNA, inhibitory DNA, steroids, and complement inhibitors.

In embodiments of the coating as described above, the first active agent is about 10% to about 50% by weight of the plurality of micro-reservoirs.

In embodiments of the coating as described above, the coating further comprises a third active agent outside of the plurality of micro-reservoirs. In some embodiments, the third active agent is selected from the group consisting of paclitaxel, sirolimus, paclitaxel derivative, sirolimus derivative, paclitaxel analogues, sirolimus analogues, inhibitory RNA, inhibitory DNA, steroids, and complement inhibitors. In some embodiments, the third active agent is the same as the first active agent.

In embodiments of the coating as described above, the hydrophobic matrix further comprises a PEG-lipid. In some embodiments, the PEG-lipid is selected from the group consisting of 1,2-distearoyl-sn-glycero-3-phosphoethanolamine-N-methoxy(polyethylene glycol)-350 (DSPE-mPEG350), 1,2-dipalmitoyl-sn-glycero-3-phosphoethanolamine-methoxy(polyethylene glycol)-350 (DPPE-mPEG350), 1,2-dioleoyl-sn-glycero-3-phosphoethanolamine-N-methoxy(polyethylene glycol)-350 (DOPE-mPEG350), 1,2-distearoyl-sn-glycero-3-phosphoethanolamine-N-methoxy(polyethylene glycol)-550 (DSPE-mPEG550), 1,2-dipalmitoyl-sn-glycero-3-phosphoethanolamine-N-methoxy(polyethylene glycol)-550 (DPPE-mPEG550), and 1,2-dioleoyl-sn-glycero-3-phosphoethanolamine-N-methoxy(polyethylene glycol)-500 (DOPE-mPEG550). In some embodiments, the PEG-lipid is about 1% to about 30% by weight of the hydrophobic matrix. In some embodiments, the PEG-lipid is about 12% or less by weight of the hydrophobic matrix.

In embodiments of the coating as described above, the coating further comprises one or more additives independently selected from penetrating enhancers and stabilizers.

In embodiments of the coating as described above, wherein the coating has a surface concentration of about 1 µg/mm² to about 10 µg/mm².

A catheter comprising an expandable portion on an elongated body, and any embodiment of the coating described above over the expandable portion. In some embodiments, the catheter further comprises a release layer between the expandable portion and the coating, wherein the release layer is configure to release the coating from the expandable portion. In some embodiments, the release layer comprises DSPE-mPEG350 or DSPE-mPEG500. In some embodiments, the release layer has a surface concentration of about 0.1 µg/mm² to about 5 µg/mm².

In embodiments of the catheter as described above, the catheter further comprises a protective coating over the coating. In some embodiments, the protective coating comprises a hydrophilic polymer, a carbohydrate, or an amphiphilic polymer. In some embodiments, the protective coating is a glycosaminoglycan or a crystalized sugar. In some embodiments, the protective coating has a surface concentration of about 0.1 µg/mm² to about 5 µg/mm².

A coating formulation for an expandable portion of a catheter comprising a solid portion and a fluid. The solid portion comprises a plurality of micro-reservoirs and at least one hydrophobic compound, wherein the plurality of micro-reservoirs comprises a first active agent and a first biodegradable or bioerodable polymer. In some embodiments, the first active agent is intermixed with or dispersed in the first biodegradable or bioerodable polymer.

In some embodiments, the plurality of micro-reservoirs further comprises a second active agent. In some embodiments, the second active agent is selected from the group consisting of paclitaxel, sirolimus, paclitaxel derivative, sirolimus derivative, paclitaxel analogues, sirolimus analogues, inhibitory RNA, inhibitory DNA, steroids, and complement inhibitors. In some embodiments, the plurality of micro-reservoirs further comprises a second biodegradable or bioerodable polymer. In some embodiments, the second biodegradable or bioerodable polymer is selected from the group consisting of polylactic acid, polyglycolic acid and their copolymers, polydioxanone, polycaprolactone, polyphosphazine, collagen, gelatin, chitosan, glycosoaminoglycans, and combination thereof.

In some embodiments of the coating formulation described above, the fluid is selected from the group consisting of pentane, hexane, heptane, heptane and fluorocarbon mixture, alcohol and fluorocarbon mixture, and alcohol and water mixture.

In some embodiments of the coating formulation described above, wherein the solid portion further comprises a third active agent outside of the plurality of micro-reservoirs. In some embodiments, the third active agent is selected from the group consisting of paclitaxel, sirolimus, paclitaxel derivative, sirolimus derivative, paclitaxel analogues, sirolimus analogues, inhibitory RNA, inhibitory DNA, steroids, and complement inhibitors.

In some embodiments of the coating formulation described above, wherein the first active agent is selected from the group consisting of paclitaxel, sirolimus, paclitaxel derivative, sirolimus derivative, paclitaxel analogues, sirolimus analogues, inhibitory RNA, inhibitory DNA, steroids, and complement inhibitors.

In some embodiments of the coating formulation described above, wherein the at least one hydrophobic compound is selected from the group consisting of sterols, lipids, phospholipids, fats, fatty acids, surfactants, and their derivatives.

In some embodiments of the coating formulation described above, wherein the at least one hydrophobic compound comprises a cholesterol and a fatty acid. In some embodiments, the weight ratio of cholesterol to fatty acid is in the range of about 1:2 to about 3:1. In some embodiments, the fatty acid is selected from the group consisting of lauric acid, lauroleic acid, tetradeadienoic acid, octanoic acid, myristic acid, myristoleic acid, decenoic acid, decanoic acid, hexadecenoic acid, palmitoleic acid, palmitic acid, linolenic acid, linoleic acid, oleic acid, vaccenic acid, stearic acid, eicosapentaenoic acid, arachadonic acid, mead acid, arachidic acid, docosahexaenoic acid, docosapentaenoic acid, docosatetraenoic acid, docosenoic acid, tetracosanoic acid, hexacosenoic acid, pristanic acid, phytanic acid, and nervonic acid.

In some embodiments of the coating formulation described above, wherein the at least one hydrophobic compound comprises a cholesterol and a phospholipid. In some embodiments, the weight ratio of cholesterol to phospholipid is in the range of about 1:2 to about 3:1. In some embodiments, the phospholipid is selected from the group consisting of phosphatidylcholine, phosphatidylethanolamine, phosphatidylserine, and phosphatidylinositol.

In some embodiments, the phospholipid is a cationic phospholipid. In some embodiments, the cationic phospholipid is phosphatidylethanolamine, dioleoylphosphatidylethanolamine (DOPE), or an amine derivative of phosphatidylcholine.

In some embodiments, the phospholipid comprises an acyl chain length of about 20 to about 34 carbons. In some embodiments, the phospholipid is selected from the group consisting of dieicosenoyl phosphatidylcholine (1,2-dieicosenoyl-sn-glycero-3-phosphocholine, C20:1 PC), diarachidonoyl phosphatidylcholine (1,2-diarachidoyl-sn-glycero-3-phosphocholine, C20:0 PC), dierucoyl phosphatidylcholine (1,2-dierucoyl-sn-glycero-3-phosphocholine, C22:1 PC), didocosahexaenoyl phosphatidylcholine (1,2-didocosahexaenoyl-sn-glycero-3-phosphocholine, C22:6 PC), heneicosenoyl phosphatidylcholine (1,2-heneicosenoyl-sn-glycero-3-phosphocholine, C21:1 PC) and dinervonyl phosphatidylcholine (1,2-dinervonoyl-sn-glycero-3-phosphocholine, C24:1 PC).

In some embodiments of the coating formulation described above, the cholesterol is DC-Cholesterol.

In some embodiments of the coating formulation described above, the solid portion further comprising a PEG-lipid, and/or an additive. In some embodiments, the PEG-lipid is selected from the group consisting of 1,2-distearoyl-sn-glycero-3-phosphoethanolamine-N-methoxy (polyethylene glycol)-350 (DSPE-mPEG350), 1,2-dipalmitoyl-sn-glycero-3-phosphoethanolamine-methoxy (polyethylene glycol)-350 (DPPE-mPEG350), 1,2-dioleoyl-sn-glycero-3-phosphoethanolamine-N-methoxy (polyethylene glycol)-350 (DOPE-mPEG350), 1,2-distearoyl-sn-glycero-3-phosphoethanolamine-N-methoxy (polyethylene glycol)-550 (DSPE-mPEG550), 1,2-dipalmitoyl-sn-glycero-3-phosphoethanolamine-N-methoxy(polyethylene glycol)-550 (DPPE-mPEG550), and 1,2-dioleoyl-sn-glycero-3-phosphoethanolamine-N-methoxy (polyethylene glycol)-500 (DOPE-mPEG550).

In some embodiments of the coating formulation described above, the plurality of micro-reservoirs is about 10% to about 75% by weight of the solid portion.

In some embodiments of the coating formulation described above, the solid portion is about 2 to about 7% by weight of the coating formulation.

A method for coating an expandable portion of a catheter comprising disposing a coating formulation of any embodiments described above over the surface of an expanded expandable portion of a catheter, evaporating the fluid, and collapsing the expandable portion. In some embodiments, disposing the coating formulation comprises spray coating, dip coating, roll coating, electrostatic deposition, printing, pipetting, or dispensing.

In some embodiments of the method described above, the method further comprises disposing a release layer on the expandable portion. In some embodiments, the release layer comprises DSPE-mPEG350 or DSPE-mPEG500.

A method for treating or preventing a condition at a treatment site comprising advancing a catheter comprising an expandable portion to the treatment site, wherein the expandable portion is coated with a coating of any embodiments described above, expanding the expandable portion to allow contact between the coating and a tissue at the treatment site, collapsing the expandable portion, and removing the catheter.

In embodiments of the method described above, the contact between the tissue and the coating results in a transfer of at least a portion of a coating on the expandable portion to the treatment site. In some embodiments, the method further comprises maintaining the contact between the coating and the tissue for a period of from about 30 to about 120 seconds.

In embodiments of any of the method described above, the condition is selected from the group consisting of atherosclerosis, stenosis or reduction in luminal diameter in a diseased blood vessel, restenosis, in-stent restenosis, and combinations thereof.

In embodiments of any of the method described above, wherein an additional release layer is disposed between the expandable portion and the coating.

What is claimed is:

1. A catheter comprising:
   an expandable portion on an elongated body; and
   a first coating over an outer surface of the expandable portion, wherein the first coating comprises:
   a hydrophobic matrix, wherein the hydrophobic matrix comprises a cholesterol and a fatty acid; and
   a dispersed phase comprising a plurality of micro-reservoirs dispersed in the hydrophobic matrix, wherein the plurality of micro-reservoirs comprises a first active agent and a biodegradable or bioerodable polymer; and
   wherein at least a portion of the first coating will transfer to a luminal surface when the expandable portion is expanded at a treatment site, and transfers at least a portion of the plurality of micro-reservoirs to the luminal surface.

2. The catheter of claim 1, wherein the weight ratio of cholesterol to fatty acid is in the range of about 1:2 to about 3:1.

3. The catheter of claim 1, wherein the fatty acid is selected from the group consisting of lauric acid, lauroleic acid, tetradeadienoic acid, octanoic acid, myristic acid, myristoleic acid, decenoic acid, decanoic acid, hexadecenoic acid, palmitoleic acid, palmitic acid, linolenic acid, linoleic acid, oleic acid, vaccenic acid, stearic acid, eicosapentaenoic acid, arachadonic acid, mead acid, arachidic acid, docosa-hexaenoic acid, docosapentaenoic acid, docosatetraenoic acid, docosenoic acid, tetracosanoic acid, hexacosenoic acid, pristanic acid, phytanic acid, and nervonic acid.

4. The catheter of claim 1, wherein the cholesterol is dimethylaminoethane-carbamoyl cholesterol (DC cholesterol).

5. The catheter of claim 1, wherein the coating comprises about 10% to about 75% by weight of the plurality of micro-reservoirs.

6. The catheter of claim 1, wherein the plurality of micro-reservoirs has an average diameter of about 1.5 microns to about 8 microns.

7. The catheter of claim 1, wherein the plurality of micro-reservoirs has an average diameter of about 2.0 microns to about 6 microns.

8. The catheter of claim 1, wherein the plurality of micro-reservoirs has an active ingredient release kinetics with a half-life of at least 14 days.

9. The catheter of claim 1, wherein the the first biodegradable or bioerodable polymer is selected from the group consisting of polylactic acid, polyglycolic acid and their copolymers, polydioxanone, polycaprolactone, polyphosphazine, collagen, gelatin, chitosan, and glycosoaminoglycans.

10. The catheter of claim 1, wherein the first active agent is selected from the group consisting of paclitaxel, sirolimus, paclitaxel derivative, sirolimus derivative, paclitaxel analogues, sirolimus analogues, inhibitory RNA, inhibitory DNA, steroids, and complement inhibitors.

11. The catheter of claim 1 wherein the hydrophobic matrix further comprises a second active agent.

12. The catheter of claim 11, wherein the second active agent is selected from the group consisting of paclitaxel, sirolimus, paclitaxel derivative, sirolimus derivative, paclitaxel analogues, sirolimus analogues, inhibitory RNA, inhibitory DNA, steroids, and complement inhibitors.

13. The catheter of claim 11, wherein the first active agent and the second active agent are the same.

14. The catheter of claim 1, wherein the active agent is about 10% to about 50% by weight of the plurality of micro-reservoirs.

15. The catheter of claim 1, further comprising a polyethylene glycol-lipid (PEG-lipid).

16. The catheter of claim 15, wherein the PEG-lipid is selected from the group consisting of 1,2-distearoyl-sn-glycero-3-phosphoethanolamine-N-methoxy(polyethylene glycol)-350 (DSPE-mPEG350), 1,2-dipalmitoyl-sn-glycero-3-phosphoethanolamine-methoxy(polyethylene glycol)-350 (DPPE-mPEG350), 1,2-dioleoyl-sn-glycero-3-phosphoethanolamine-N-methoxy(polyethylene glycol)-350 (DOPE-mPEG350), 1,2-distearoyl-sn-glycero-3-phosphoethanolamine-N-methoxy(polyethylene glycol)-550 (DSPE-mPEG550), 1,2-dipalmitoyl-sn-glycero-3-phosphoethanolamine-N-methoxy(polyethylene glycol)-550 (DPPE-mPEG550), and 1,2-dioleoyl-sn-glycero-3-phosphoethanolamine-N-methoxy(polyethylene glycol)-500 (DOPE-mPEG550).

17. The catheter of claim 15, wherein the PEG-lipid is about 1% to about 10% by weight of the solids of the hydrophobic matrix.

18. The catheter of claim 1, further comprising one or more additives independently selected from penetrating enhancers and stabilizers.

19. The catheter of claim 1, wherein the coating has a surface concentration of about 1 µg/mm$^2$ to about 10 µg/mm$^2$.

20. A catheter comprising:
an expandable portion on an elongated body;
a first coating of claim 1 over the expandable portion; and
a release layer between the expandable portion and the coating, wherein at least a portion of the first coating will be released from the expandable portion when the expandable portion is expanded at a treatment site.

21. The catheter of claim 20, wherein the release layer comprises DSPE-mPEG350 or DSPE-mPEG500.

22. The catheter of claim 20, wherein the release layer has a surface concentration of about 0.1 µg/mm² to about µg/mm².

23. The catheter of claim 20, further comprising a second protective coating over the first coating.

24. The catheter of claim 20, wherein the protective coating comprises a hydrophilic polymer, a carbohydrate, or an amphiphilic polymer.

25. The catheter of claim 23, wherein the protective coating is a glycosaminoglycan or a crystallized sugar.

26. The catheter of claim 23, wherein the protective coating has a surface concentration of about 0.1 µg/mm² to about 5 µg/mm².

27. A method for coating an expandable portion of a catheter such that at least a portion of the coating transfers to a luminal surface at a treatment site upon expansion of the expandable portion, the method comprises:
disposing a coating formulation onto the surface of an expanded expandable portion of the catheter wherein the coating formulation comprises:
a plurality of micro-reservoirs, wherein the plurality of micro-reservoirs comprise a first active agent intermixed with or dispersed in a biodegradable or bioerodable polymer;
at least one hydrophobic compound wherein the hydrophobic compound comprises a cholesterol and a fatty acid or a cholesterol and a phospholipid, wherein the phospholipid comprises an acyl chain phospholipid with an acyl chain length of about 20 to about 34; and
a fluid, wherein the fluid is selected from the group consisting of pentane, hexane, heptane, heptane, and fluorocarbon mixture, alcohol and fluorocarbon mixture, and alcohol and water mixture; and
evaporating the fluid; and
collapsing the expandable portion; and
wherein the plurality of micro-reservoirs are dispersed in a hydrophobic matrix formed by the at least one hydrophobic compound.

28. The method of claim 27 wherein the plurality of micro-reservoirs is about 10% to about 75% by weight of the solids of the coating formulation.

29. The method of claim 27, wherein the coating formulation further comprises a second active agent outside of the plurality of micro-reservoirs.

30. The method of claim 27, wherein the active agent is selected from the group consisting of paclitaxel, sirolimus, paclitaxel derivative, sirolimus derivative, paclitaxel analogues, sirolimus analogues, inhibitory RNA, inhibitory DNA, steroids, and complement inhibitors.

31. The method of claim 27, wherein the at least one hydrophobic compound comprises a cholesterol and a fatty acid.

32. The method of claim 31 wherein the weight ratio of cholesterol to fatty acid is in the range of about 1:2 to about 3:1.

33. The method of claim 31, wherein the fatty acid is selected from the group consisting of lauric acid, lauroleic acid, tetradeadienoic acid, octanoic acid, myristic acid, myristoleic acid, decenoic acid, decanoic acid, hexadecenoic acid, palmitoleic acid, palmitic acid, linolenic acid, linoleic acid, oleic acid, vaccenic acid, stearic acid, eicosapentaenoic acid, arachadonic acid, mead acid, arachidic acid, docosahexaenoic acid, docosapentaenoic acid, docosatetraenoic acid, docosenoic acid, tetracosanoic acid, hexacosenoic acid, pristanic acid, phytanic acid, and nervonic acid.

34. The method of claim 27 wherein the at least one hydrophobic compound comprises a cholesterol and a phospholipid, wherein the phospholipid comprises an acyl chain phospholipid with an acyl chain length of about 20 to about 34.

35. The method of claim 34 wherein the weight ratio of cholesterol to phospholipid is in the range of about 1:2 to 3:1.

36. The method of claim 34 wherein the phospholipid is dinervonicphosphatidylcholine, heneicosenoylphosphatidylcholine, or dierucoylphosphatidylcholine.

37. The method of claim 27 wherein the cholesterol is dimethylaminoethane-carbamoyl cholesterol (DC cholesterol).

38. The method of claim 27, wherein the solids content comprising a plurality of micro-reservoirs and at least one hydrophobic compound has a weight concentration of about 2 to 7%.

39. The method of claim 27, wherein the coating formulation further comprises a polyethylene glycol-lipid (PEG-lipid).

40. The method of claim 27, wherein disposing the formula comprises spray coating, dip coating, roll coating, electrostatic deposition, printing, pipetting, or dispensing.

41. The method of claim 27, wherein an additional release layer is disposed between the expandable portion and the coating.

42. A method for treating or preventing a condition at a treatment site, wherein the condition is selected from the group consisting of atherosclerosis, stenosis or reduction in luminal diameter in a diseased blood vessel, restenosis, and in-stent restenosis, comprising:
advancing a catheter of claim 1 to the treatment site, wherein the coating comprises an effective amount of the first active agent for treating or preventing the condition;
expanding the expandable portion to allow contact between the coating and a tissue at the treatment site;
collapsing the expandable portion; and
removing the catheter.

43. The method of claim 42, wherein the contact between the tissue and the coating results in a transfer of at least a portion of a coating on the expandable portion to the treatment site.

44. The method of claim 42, further comprising maintaining the contact between the expandable portion and the coating for a period of from about 30 to about 120 seconds.

* * * * *

UNITED STATES PATENT AND TRADEMARK OFFICE
CERTIFICATE OF CORRECTION

PATENT NO. : 10,098,987 B2
APPLICATION NO. : 15/290931
DATED : October 16, 2018
INVENTOR(S) : Michael Thomas Ahlering It is certified that error appears in the above-identified patent and that said Letters Patent is hereby corrected as shown below:

In the Specification

In Column 5, Line 4, Column 29, Line 42, Column 32, Line 12 (Approx.), Column 33, Line 63, Claim 3, and Column 36, Line 6, Claim 33, change "tetradeadienoic" to --tetradecadienoic--.

In Column 5, Line 8, Column 29, Line 46, Column 32, Line 17 (Approx.), Column 33, Line 67, Claim 3, and Column 36, Line 10 (Approx.), Claim 33, change "arachadonic" to --arachidonic--.

In Column 6, Line 15 and 16, Column 30, Lines 8 and 8-9 and Column 32, Lines 46 and 46-47, change "heneicosenoyl" to --heneicosanoyl--.

In Column 6, Line 18, change "PC)" to --PC).--.

In Column 7, Line 19, Column 29, Line 28, Column 30, Lines 32-33, Column 31, Lines 47-48, and Column 34, Lines 24-25, Claim 9, change "glycosoaminoglycans," to --glycosaminoglycans,--.

In Column 8, Lines 27, 30, and 37-38, change "hemocompatiblity." to --hemocompatibility.--.

In Column 8, Lines 52 and 58, and Column 32, Lines 61-62, change "di stearoyl" to --distearoyl--.

In Column 13, Lines 27-28, change "(Microspheres) sphere s)" to --(Microspheres)--.

In Column 28, Line 18 (Approx.), change "bloodstream" to --bloodstream.--.

In the Claims

In Column 34, Line 20, Claim 9, change "the the" to --the--.

In Column 35, Line 11, Claim 22, change "about" to --about 5--.

Signed and Sealed this
Ninth Day of April, 2019

Andrei Iancu
*Director of the United States Patent and Trademark Office*

CERTIFICATE OF CORRECTION (continued)
U.S. Pat. No. 10,098,987 B2

In Column 35, Line 15, Claim 24, change "20," to --23,--.

In Column 35, Line 41, Claim 27, change "heptane, heptane," to --heptane,--.

In Column 36, Lines 24-25 (Approx.), Claim 36, change "heneicosenoylphosphatidylcholine," to --heneicosanoylphosphatidylcholine,--.